(12) United States Patent
Holoboski et al.

(10) Patent No.: US 7,960,378 B2
(45) Date of Patent: Jun. 14, 2011

(54) THERAPEUTIC COMPOUNDS

(75) Inventors: Mark Holoboski, Irvine, CA (US);
Robert M. Burk, Laguna Beach, CA (US); Mari Posner, Laguna Niguel, CA (US)

(73) Assignee: Allergan, Inc., Irvine, CA (US)

( * ) Notice: Subject to any disclaimer, the term of this patent is extended or adjusted under 35 U.S.C. 154(b) by 270 days.

(21) Appl. No.: 12/405,349

(22) Filed: Mar. 17, 2009

(65) Prior Publication Data
US 2009/0239930 A1 Sep. 24, 2009

Related U.S. Application Data

(60) Provisional application No. 61/037,622, filed on Mar. 18, 2008.

(51) Int. Cl.
*A61K 31/535* (2006.01)
*A61K 31/38* (2006.01)
*C07D 333/24* (2006.01)
*C07D 413/12* (2006.01)

(52) U.S. Cl. ............... 514/231.5; 514/448; 544/145; 549/79

(58) Field of Classification Search .......... 544/145; 514/231.5, 448; 549/79
See application file for complete search history.

(56) References Cited

U.S. PATENT DOCUMENTS

| | | | |
|---|---|---|---|
| 4,166,452 | A | 9/1979 | Generales |
| 4,256,108 | A | 3/1981 | Theeuwes |
| 4,265,874 | A | 5/1981 | Bonsen |
| 5,476,872 | A | 12/1995 | Garst et al. |
| 6,110,969 | A | 8/2000 | Tani |
| 6,376,533 | B1 | 4/2002 | Burk et al. |
| 6,410,591 | B1 | 6/2002 | Burk et al. |
| 6,437,146 | B1 | 8/2002 | Hattori |
| 6,710,072 | B2 | 3/2004 | Burk |
| 2006/0135609 | A1 | 6/2006 | Toon et al. |
| 2007/0254920 | A1 | 11/2007 | Delong et al. |
| 2007/0270387 | A1 | 11/2007 | Donde et al. |

FOREIGN PATENT DOCUMENTS

| | | |
|---|---|---|
| BE | 900 959 | 5/1985 |
| WO | WO 2006-096179 | 9/2006 |
| WO | WO 2008/041054 | 4/2008 |
| WO | WO 2008/073752 | 6/2008 |

OTHER PUBLICATIONS

Carey, Francis A.: Conformations of Alkanes and Cycloalkanes. Organic Chemistry, New York: McGraw-Hill Book Company 1987, p. 63.
Chourasia, M.K.; et al.: Pharmaceutical Approaches to Colon Targeted Drug Delivery Systems. J. Pharm Pharmaceut Sci 6 (1): 33-66, 2003.
Kousuke, T.; et al.: Development of a Highly Selective EP2-Receptor Agonist. Part 1: Identification of 16-Hydroxy-17,17-Trimethylene PGE2 Derivatives. Bioorg. Med. Chem. 2002, 10, 1093.
Remington's Pharmaceutical Sciences, Mack Publishing Company, Easton, Pa., 16th Edition, 1980.
Shareef et al.: Clonic Drug Delivery: An Updated Review. AAPS PharmSci 2003; 5(2) Article 17.
U.S. Appl. No. 60/744,236, filed Apr. 4, 2006, Donde.

*Primary Examiner* — Rebecca L Anderson
(74) *Attorney, Agent, or Firm* — Kevin J. Forrestal; John E. Wurst; Doina G. Ene

(57) ABSTRACT

Compounds comprising

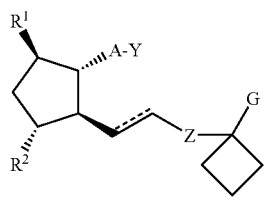

or a pharmaceutically acceptable salt or a prodrug thereof, are disclosed, wherein Y, A, $R^1$, $R^2$, Z, and G are as described. Methods, compositions, and medicaments related thereto are also disclosed.

14 Claims, No Drawings

THERAPEUTIC COMPOUNDS

RELATED APPLICATION

This application claims the benefit of U.S. Provisional Application Ser. No. 61/037,622, filed Mar. 18, 2008, the disclosure of which is hereby incorporated in its entirety herein by reference.

DESCRIPTION OF RELATED ART

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical β-adrenoreceptor antagonists have traditionally been the drugs of choice for treating glaucoma.

Certain eicosanoids and their derivatives are currently commercially available for use in glaucoma management. Eicosanoids and derivatives include numerous biologically important compounds such as prostaglandins and their derivatives. Prostaglandins can be described as derivatives of prostanoic acid which have the following structural formula:

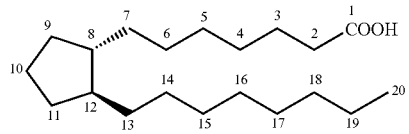

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostagiandin $E_1$ ($PGE_1$), prostaglandin $E_2$ ($PGE_2$)], and on the configuration of the substituents on the alicyclic ring indicated by α or β [e.g. prostaglandin $F_{2\alpha}$ ($PGF_{2\beta}$)].

Prostaglandin $EP_2$ selective agonists are believed to have several medical uses. For example, U.S. Pat. No. 6,437,146 teaches the use of prostaglandin $EP_2$ selective agonists "for treating or preventing inflammation and pain in joint and muscle (e.g., rheumatoid arthritis, rheumatoid spondylitis, osteoarthritis, gouty arthritis, juvenile arthritis, etc.), inflammatory skin condition (e.g., sunburn, burns, eczema, dermatitis, etc.), inflammatory eye condition (e.g., conjunctivitis, etc.), lung disorder in which inflammation is involved (e.g., asthma, bronchitis, pigeon fancier's disease, farmer's lung, etc.), condition of the gastrointestinal tract associated with inflammation (e.g., aphthous ulcer, Chrohn's disease, atrophic gastritis, gastritis varialoforme, ulcerative colitis, coeliac disease, regional ileitis, irritable bowel syndrome, etc.), gingivitis, inflammation, pain and tumescence after operation or injury, pyrexia, pain and other conditions associated with inflammation, allergic disease, systemic lupus crythematosus, scleroderma, polymyositis, tendinitis, bursitis, periarteritis nodose, rheumatic fever, Sjgren's syndrome, Behcet disease, thyroiditis, type I diabetes, diabetic complication (diabetic microangiopathy, diabetic retinopathy, diabetic neohropathy, etc.), nephrotic syndrome, aplastic anemia, myasthenia gravis, uveitis contact dermatitis, psoriasis, Kawasaki disease, sarcoidosis, Hodgkin's disease, Alzheimers disease, kidney dysfunction (nephritis, nephritic syndrome, etc.), liver dysfunction (hepatitis, cirrhosis, etc.), gastrointestinal dysfunction (diarrhea, inflammatory bowel disease, etc.) shock, bone disease characterized by abnormal bone metabolism such as osteoporosis (especially, postmenopausal osteoporosis), hypercalcemia, hyperparathyroidism, Paget's bone diseases, osteolysis, hypercalcemia of malignancy with or without bone metastases, rheumatoid arthritis, periodonritis, osteoarthritis, ostealgia, osteopenia, cancer cachexia, calculosis, lithiasis (especially, urolithiasis), solid carcinoma, mesangial proliferative glomerulonephritis, edema (e.g. cardiac edema, cerebral edema, etc.), hypertension such as malignant hypertension or the like, premenstrual tension, urinary calculus, oliguria such as the one caused by acute or chronic failure, hyperphosphaturia, or the like."

U.S. Pat. No 6,710,072 teaches the use of EP2 agonists for the treatment or prevention of "osteoporosis, constipation, renal disorders, sexual dysfunction, baldness, diabetes, cancer and in disorder of immune regulation . . . various pathophysiological diseases including acute myocardial infarction, vascular thrombosis, hypertension, pulmonary hypertension, ischemic heart disease, congestive heart failure, and angina pectoris."

SUMMARY

Disclosed herein are compounds useful in treating glaucoma, inflammatory bowel disease, baldness, the stimulation of hair growth, and the stimulation of the conversion of vellus hair to terminal hair. The compounds themselves are disclosed below.

DESCRIPTION OF THE INVENTION

Disclosed herein is a compound for administration to a mammal for the treatment of glaucoma, ocular hypertension, or baldness in a mammal, wherein the compound is described herein.

Disclosed herein is a method comprising administering a compound to a mammal for the treatment of glaucoma, ocular hypertension, or baldness in a mammal, wherein the compound is described herein.

Another embodiment is use of a compound in the manufacture of a medicament for the treatment of glaucoma, ocular hypertension, or baldness in a mammal, wherein the compound is described herein.

Another embodiment is a composition comprising a compound described herein, wherein the composition is a liquid which is ophthalmically acceptable.

Another embodiment is a kit comprising a composition comprising a compound disclosed herein, a package for dispensing drops of the composition, and a label indicating that said composition is to be administered topically to the eye of a mammal for the treatment of glaucoma or ocular hypertension in a mammal.

The compounds are described generally by the formula

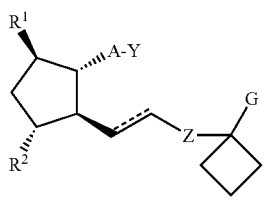

or a pharmaceutically acceptable salt, or a prodrug thereof; Y is

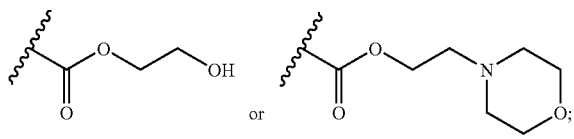

A is —$(CH_2)_6$—, cis —$CH_2CH$=$CH$—$(CH_2)_3$—, or —$CH_2C$≡$C$—$(CH_2)_3$—, wherein 1 or 2 carbon atoms may be replaced by S or O; or A is —$(CH_2)_m$—Ar—$(CH_2)_o$— wherein Ar is interarylene or heterointerarylene, the sum of m and o is 1, 2, 3, or 4, and wherein one $CH_2$ may be replaced by S or O;

$R^1$ is CN or OH;

$R^2$ is H, CN, OH, F, Cl, Br, or $CH_3$ with the proviso that if $R^1$ is OH, $R^2$ is not OH;

Z is $CH_2CHOH$, $CHOHCH_2$, or CHOH;

G is L, $CH_2L$, OL, or SL;

L is phenyl, monocyclic heteroaryl, or $C_{1-6}$ alkyl.

A person of ordinary skill in the art understands the meaning of the stereochemistry associated with the hatched wedge/solid wedge structural features. For example, an introductory organic chemistry textbook (Francis A. Carey, Organic Chemistry, New York: McGraw-Hill Book Company 1987, p. 63) states "a wedge indicates a bond coming from the plane of the paper toward the viewer" and the hatched wedge, indicated as a "dashed line", "represents a bond receding from the viewer."

In relation to the identity of A disclosed in the chemical structures presented herein, A is —$(CH_2)_6$—, cis —$CH_2CH$=$CH$—$(CH_2)_3$—, or —$CH_2C$≡$C$—$(CH_2)_3$—, wherein 1 or 2 carbon atoms may be replaced with S or O; or A is —$(CH_2)_m$—Ar—$(CH_2)_o$— wherein Ar is interarylene or heterointerarylene, the sum of m and o is 1, 2, 3, or 4, and wherein one $CH_2$ may be replaced with S or O.

While not intending to be limiting, A may be —$(CH_2)_6$—, cis —$CH_2CH$=$CH$—$(CH_2)_3$—, or —$CH_2C$≡$C$—$(CH_2)_3$—.

Alternatively, A may be a group which is related to one of these three moieties in that any carbon is replaced with S and/or O. For example, while not intending to limit the scope of the invention in any way, A may be a moiety where S replaces one or two carbon atoms such as one of the following or the like.

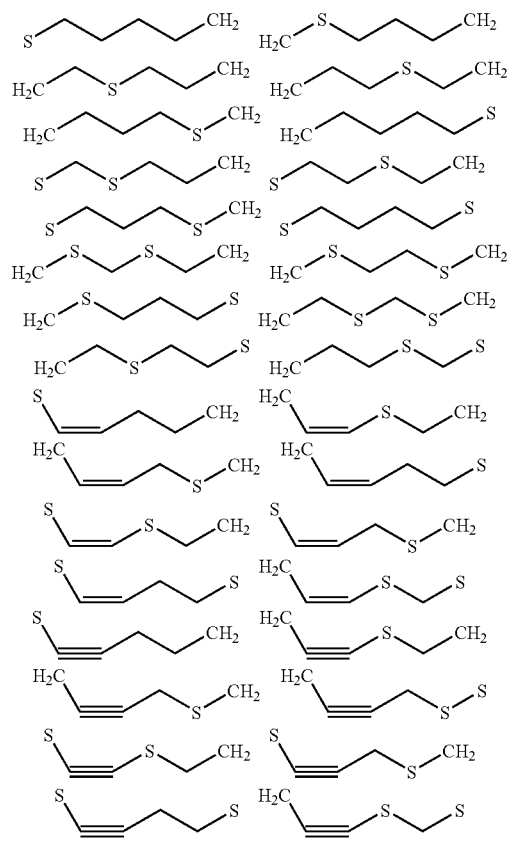

Alternatively, while not intending to limit the scope of the invention in any way, A may be a moiety where O replaces one or two carbon atoms such as one of the following or the like.

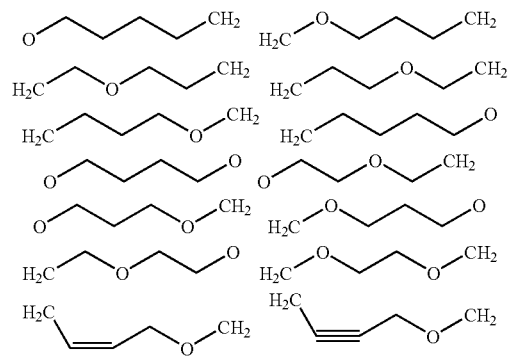

Alternatively, while not intending to limit the scope of the invention in any way, A may have an O replacing one carbon atom and an S replacing another carbon atom, such as one of the following or the like.

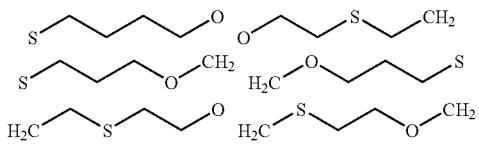

Alternatively, while not intending to limit the scope of the invention in any way, in certain embodiments A is —(CH$_2$)$_m$—Ar—(CH$_2$)$_o$— wherein Ar is interarylene or heterointerarylene, the sum of m and o is 1, 2, 3, or 4, and wherein one CH$_2$ may be replaced with S or O. In other words, while not intending to limit the scope of the invention in any way, in one embodiment A comprises 1, 2, 3, or 4 CH$_2$ moieties and Ar, e.g. —CH$_2$—Ar—, —(CH$_2$)$_2$—Ar—, —CH$_2$—Ar—CH$_2$—, —CH$_2$Ar—(CH$_2$)$_2$—, —(CH$_2$)$_2$—Ar—(CH$_2$)$_2$—, and the like;

in another embodiment A comprises O, 0, 1, 2, or 3 CH$_2$ moieties, and Ar, e.g., —O—Ar—, Ar—CH$_2$—O—, —O—Ar—(CH$_2$)$_2$—, —O—CH$_2$—Ar—, —O—CH$_2$—Ar—(CH$_2$)$_2$, and the like; or in another embodiment A comprises S, 0, 1, 2, or 3 CH$_2$ moieties, and Ar, e.g., —S—Ar—, Ar—CH$_2$—S—, —S—Ar—(CH$_2$)$_2$—, —S—CH$_2$—Ar—, —S—CH$_2$—Ar—(CH$_2$)$_2$, —(CH$_2$)$_2$—S—Ar, and the like.

In another embodiment, the sum of m and o is 2, 3, or 4 wherein one CH$_2$ may be replaced with S or O.

In another embodiment, the sum of m and o is 3 wherein one CH$_2$ may be replaced with S or O.

In another embodiment, the sum of m and o is 2 wherein one CH$_2$ may be replaced with S or O.

In another embodiment, the sum of m and o is 4 wherein one CH$_2$ may be replaced with S or O.

Interarylene or heterointerarylene refers to an aryl ring or ring system or a heteroaryl ring or ring system which connects two other parts of a molecule, i.e. the two parts are bonded to the ring in two distinct ring positions. Interarylene or heterointerarylene may be substituted or unsubstituted. Unsubstituted interarylene or heterointerarylene has no substituents other than the two parts of the molecule it connects. Substituted interarylene or heterointerarylene has substituents in addition to the two parts of the molecule it connects.

In one embodiment, Ar is substituted or unsubstituted interphenylene, interthienylene, interfurylene, interpyridinylene, interoxazolylene, and interthiazolylene. In another embodiment Ar is interphenylene (Ph). In another embodiment A is —(CH$_2$)$_2$—Ph—. Substituents may have 4 or less heavy atoms, wherein the heavy atoms are C, N, O, S, P, F, Cl, Br, and/or I in any stable combination. Any number of hydrogen atoms required for a particular substituent will also be included. A substituent must be stable enough for the compound to be useful as described herein. In addition to the atoms listed above, a substituent may also have a metal cation or any other stable cation having an atom not listed above if the substituent is acidic and the salt form is stable. For example, —OH may form an —O$^-$Na$^+$ salt or CO$_2$H may form a CO$_2^-$K$^+$ salt. Any cation of the salt is not counted in the "4 or less heavy atoms." Thus, the substituent may be hydrocarbyl having up to 4 carbon atoms, including alkyl up to C$_4$, alkenyl, alkynyl, and the like;

hydrocarbyloxy up to C$_3$;

organic acid such as CO$_2$H, SO$_3$H, P(O)(OH)$_2$, and the like, and salts thereof;

CF$_3$;

halo, such as F, Cl, or Br;

hydroxyl;

NH$_2$ and alkylamine functional groups up to C$_3$;

other N or S containing substituents such as CN, NO$_2$, and the like;

and the like.

In one embodiment A is —(CH$_2$)$_m$—Ar—(CH$_2$)$_o$— wherein Ar is interphenylene, the sum of m and o is 1, 2, or 3, and wherein one CH$_2$ may be replaced with S or O.

In another embodiment A is —CH$_2$—Ar—OCH$_2$—. In another embodiment A is —CH$_2$—Ar—OCH$_2$— and Ar is interphenylene. In another embodiment, Ar is attached at the 1 and 3 positions, otherwise known as m-interphenylene, such as when A has the structure shown below.

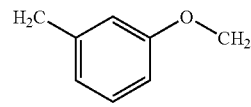

In another embodiment A is —(CH$_2$)$_6$—, cis —CH$_2$CH=CH—(CH$_2$)$_3$—, or —CH$_2$C≡C—(CH$_2$)$_3$—, wherein 1 or 2 carbon atoms may be replaced with S or O; or A is —(CH$_2$)$_2$—Ph— wherein one CH$_2$ may be replaced with S or O.

In another embodiment A is —(CH$_2$)$_6$—, cis —CH$_2$CH=CH—(CH$_2$)$_3$—, or —CH$_2$C≡C—(CH$_2$)$_3$—, wherein 1 or 2 carbon atoms may be replaced with S or O; or A is —(CH$_2$)$_2$—Ph—.

In other embodiments, A has one of the following structures, where Y is attached to the aromatic or heteroaromatic ring.

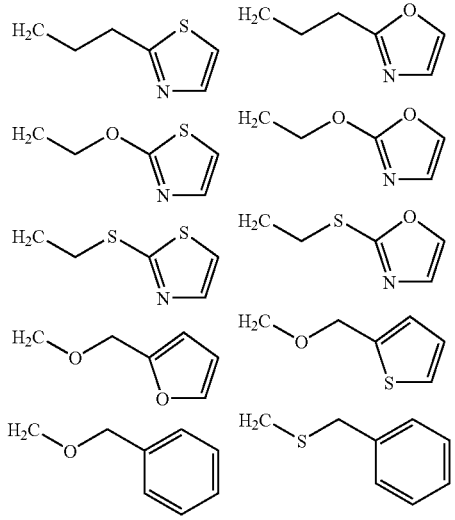

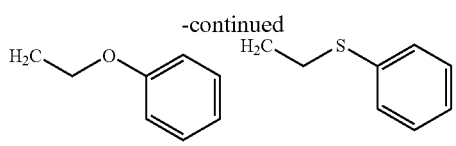

In another embodiment A is —CH$_2$OCH$_2$Ar.
In another embodiment A is —CH$_2$SCH$_2$Ar.
In another embodiment A is —(CH$_2$)$_3$Ar.
In another embodiment A is —CH$_2$O(CH$_2$)$_4$.
In another embodiment A is —CH$_2$S(CH$_2$)$_4$.
In another embodiment A is —(CH$_2$)$_6$—.
In another embodiment A is cis —CH$_2$CH=CH—(CH$_2$)$_3$—.
In another embodiment A is —CH$_2$C≡C—(CH$_2$)$_3$—.
In another embodiment A is —S(CH$_2$)$_3$S(CH$_2$)$_2$—.
In another embodiment A is —(CH$_2$)$_4$OCH$_2$—.
In another embodiment A is cis —CH$_2$CH=CH—CH$_2$OCH$_2$—.
In another embodiment A is —CH$_2$CH≡CH—CH$_2$OCH$_2$—.
In another embodiment A is —(CH$_2$)$_2$S(CH$_2$)$_3$—.
In another embodiment A is —CH$_2$—Ph—OCH$_2$—, wherein Ph is interphenylene.
In another embodiment A is —CH$_2$-mPh—OCH$_2$—, wherein mPh is m-interphenylene.
In another embodiment A is —CH$_2$—O—(CH2)$_4$—.
In another embodiment A is —CH$_2$—O—CH$_2$—Ar—, wherein Ar is 2,5-interthienylene.
In another embodiment A is —CH$_2$—O—CH$_2$—Ar—, wherein Ar is 2,5-interfurylene.

Compounds according to the each of the structures depicted below, and pharmaceutically acceptable salts thereof, and prodrugs thereof, are contemplated as individual embodiments. In other words, each structure represents a different embodiment.

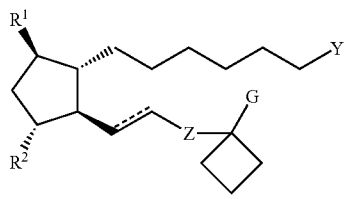

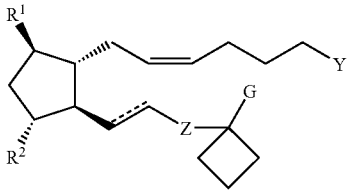

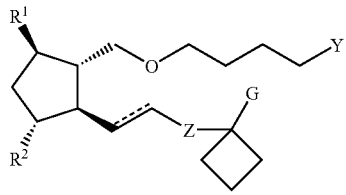

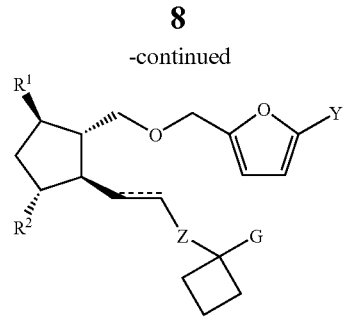

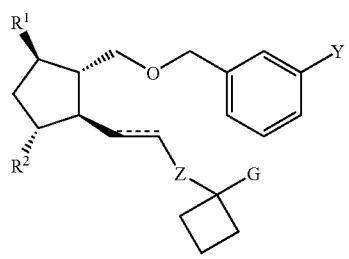

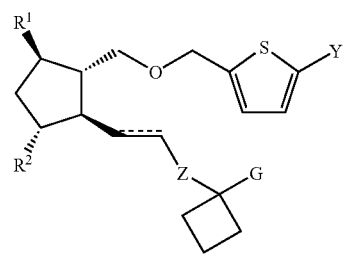

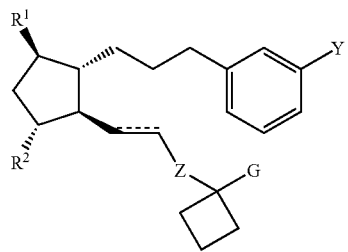

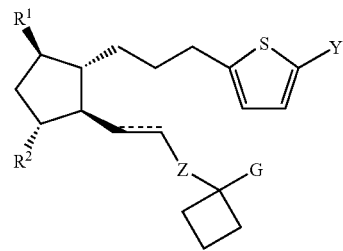

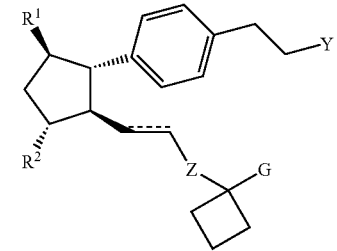

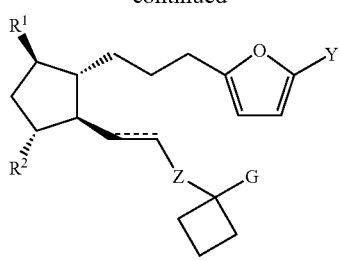

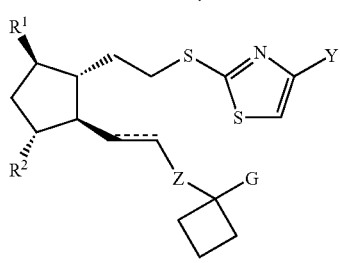

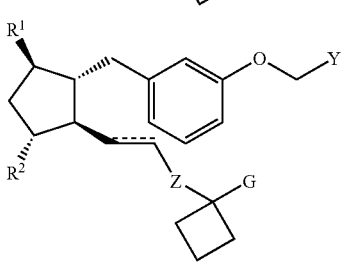

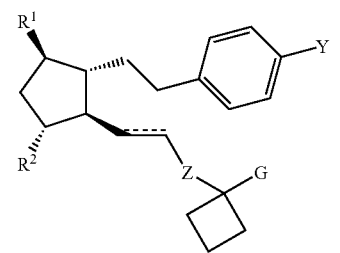

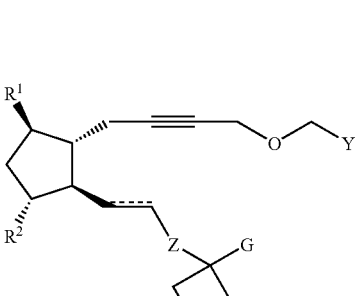

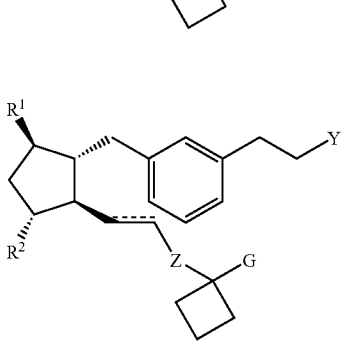

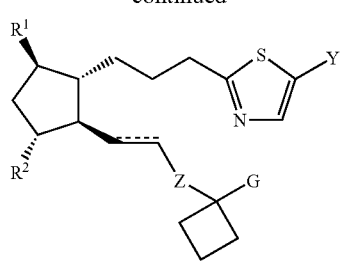

$R^1$ is CN or OH. Thus, compounds according to the each of the structures depicted below, and pharmaceutically acceptable salts thereof, and prodrugs thereof, are contemplated as individual embodiments. In other words, each structure represents a different embodiment.

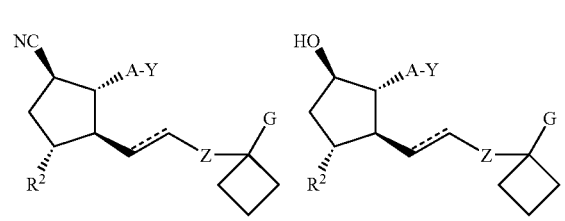

$R^2$ is H, CN, OH, F, Cl, Br, or $CH_3$ with the proviso that if $R^1$ is OH, $R^2$ is not OH. Thus, compounds according to the each of the structures depicted below, and pharmaceutically acceptable salts thereof, and prodrugs thereof, are contemplated as individual embodiments. In other words, each structure represents a different embodiment.

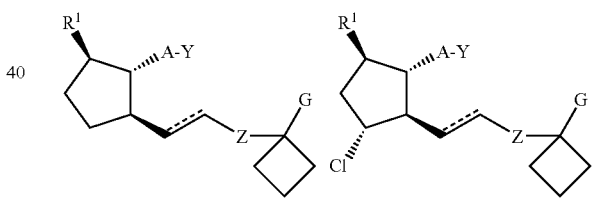

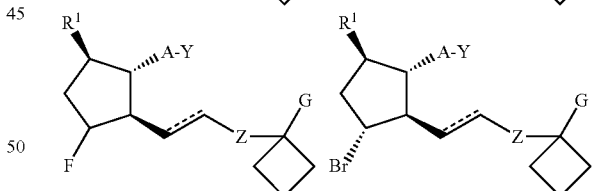

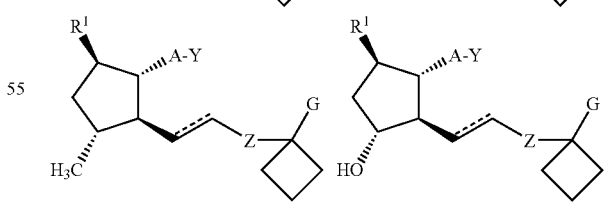

Z is $CH_2CHOH$, $CHOHCH_2$, or CHOH. Thus, compounds according to the each of the structures depicted below, and pharmaceutically acceptable salts thereof, and prodrugs thereof, are contemplated as individual embodiments. In other words, each structure represents a different embodiment.

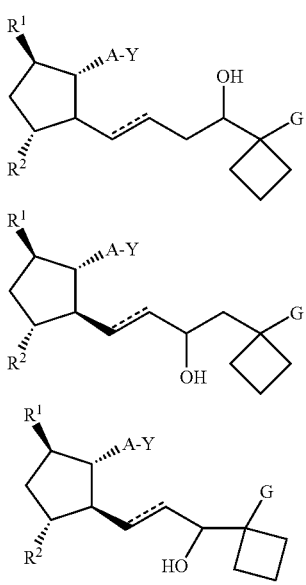

G is L, CH$_2$L, OL, or SL. Thus, compounds according to the each of the structures depicted below, and pharmaceutically acceptable salts thereof, and prodrugs thereof, are contemplated as individual embodiments. In other words, each structure represents a different embodiment.

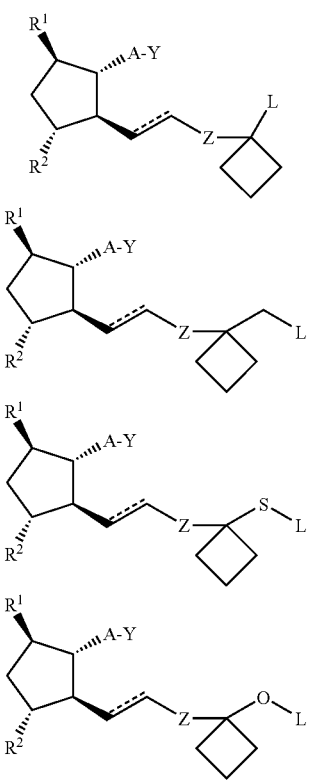

L is phenyl or monocyclic heteroaryl, or C$_{1-6}$ alkyl. Phenyl or monocyclic heteroaryl may be substituted or unsubstituted. If L is substituted, it has 1, 2, 3, or 4 heavy atoms, wherein the heavy atoms are C, N, O, S, P, F, Cl, Br, and/or I in any stable combination. That is, the possible substituents on phenyl or heterocyclic aryl are the same as those on interarylene or interheteroarylene, and like interarylene and heterointerarylene, the substituents may be the same or different with respect to one another. Likewise, the substituents on Ar and L may be the same or different with respect to one another. In particular phenyl, thienyl, furyl, and pyridinyl, either substituted or unsubstituted, are contemplated.

C$_{1-6}$ alkyl is alkyl having 1, 2, 3, 4, 5, or 6 carbon atoms. Alkyl is a moiety having only carbon and hydrogen and no double bonds. In one embodiment G, is ethyl.

COMPOSITION EXAMPLE

A composition comprising a compound according to any structure disclosed herein, wherein the composition is a liquid which is ophthalmically acceptable.

KIT EXAMPLE

Another embodiment is a kit comprising a composition comprising a compound according to any structure disclosed herein, a package for dispensing drops of the composition, and a label indicating that said composition is to be administered topically to the eye of a mammal for the treatment of glaucoma or ocular hypertension in a mammal.

METHOD EXAMPLE

A method comprising administering a compound according to any structure disclosed herein to a mammal for the treatment of glaucoma or ocular hypertension in a mammal.

MEDICAMENT EXAMPLES

Use of a compound according to any structure disclosed herein in the manufacture of a medicament for the treatment of glaucoma or ocular hypertension in a mammal. A medicament comprising a compound according to any structure disclosed herein for the treatment of glaucoma or ocular hypertension in a mammal.

A "pharmaceutically acceptable salt" is any salt that retains the activity of the parent compound and does not impart any additional deleterious or untoward effects on the subject to which it is administered and in the context in which it is administered compared to the parent compound. A pharmaceutically acceptable salt also refers to any salt which may form in vivo as a result of administration of an acid, another salt, or a prodrug which is converted into an acid or salt.

Pharmaceutically acceptable salts of acidic functional groups may be derived from organic or inorganic bases. The salt may comprise a mono or polyvalent ion. Of particular interest are the inorganic ions lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

A "prodrug" is a compound which is converted to a therapeutically active compound after administration, and the term should be interpreted as broadly herein as is generally understood in the art. While not intending to limit the scope of the invention, conversion may occur by hydrolysis of an ester group or some other biologically labile group. Generally, but not necessarily, a prodrug is inactive or less active than the therapeutically active compound to which it is converted. Ester prodrugs of the compounds disclosed herein are specifically contemplated. An ester may be derived from a carboxylic acid of C1 (i.e. the terminal carboxylic acid of a natural prostaglandin), or an ester may be derived from a carboxylic acid functional group on another part of the molecule, such as on a phenyl ring. While not intending to be limiting, an ester may be an alkyl ester, an aryl ester, or a heteroaryl ester. The term alkyl has the meaning generally understood by those skilled in the art and refers to linear, branched, or cyclic alkyl moieties. $C_{1-6}$ alkyl esters are particularly useful, where alkyl part of the ester has from 1 to 6 carbon atoms and includes, but is not limited to, methyl, ethyl, propyl, isopropyl, n-butyl, sec-butyl, isobutyl, t-butyl, pentyl isomers, hexyl isomers, cyclopropyl, cyclobutyl, cyclopentyl, cyclohexyl, and combinations thereof having from 1-6 carbon atoms, etc.

Those skilled in the art will readily understand that for administration or the manufacture of medicaments the compounds disclosed herein can be admixed with pharmaceutically acceptable excipients which per se are well known in the art. Specifically, a drug to be administered systemically, it may be confected as a powder, pill, tablet or the like, or as a solution, emulsion, suspension, aerosol, syrup or elixir suitable for oral or parenteral administration or inhalation.

For solid dosage forms or medicaments, non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate. The solid dosage forms may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release. Liquid pharmaceutically administrable dosage forms can, for example, comprise a solution or suspension of one or more of the presently useful compounds and optional pharmaceutical adjutants in a carrier, such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 16th Edition, 1980. The composition of the formulation to be administered, in any event, contains a quantity of one or more of the presently useful compounds in an amount effective to provide the desired therapeutic effect.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

The amount of the presently useful compound or compounds administered is dependent on the therapeutic effect or effects desired, on the specific mammal being treated, on the severity and nature of the mammal's condition, on the manner of administration, on the potency and pharmacodynamics of the particular compound or compounds employed, and on the judgment of the prescribing physician. The therapeutically effective dosage of the presently useful compound or compounds may be in the range of about 0.5 or about 1 to about 100 mg/kg/day.

Ophthalmic Applications

A liquid which is ophthalmically acceptable is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions of the present invention include, but are not limited to, benzalkonium chloride, chlorobutanol, thimerosal, phenylmercuric acetate and phenylmercuric nitrate. A useful surfactant is, for example, Tween 80. Likewise, various useful vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. A useful chelating agent is edetate disodium, although other chelating agents may also be used in place or in conjunction with it.

The ingredients are usually used in the following amounts:

| Ingredient | Amount (% w/v) |
| --- | --- |
| active ingredient | about 0.001-5 |
| preservative | 0-0.10 |
| vehicle | 0-40 |

-continued

| Ingredient | Amount (% w/v) |
|---|---|
| tonicity adjustor | 1-10 |
| buffer | 0.01-10 |
| pH adjustor | q.s. pH 4.5-7.5 |
| antioxidant | as needed |
| surfactant | as needed |
| purified water | as needed to make 100% |

Applications for Stimulating Hair Growth

In one embodiment, the compounds disclosed herein can be useful in the treatment of baldness and/or hair loss. Alopecia (baldness) is a deficiency of either normal or abnormal hair, and is primarily a cosmetic problem in humans. It is a deficiency of terminal hair, the broad diameter, colored hair that is readily seen. However, in the so called bald person, although there is a noticeable absence of terminal hair, the skin does contain vellus hair, which is a fine colorless hair which may require microscopic examination to determine its presence. This vellus hair is a precursor to terminal hair.

The compounds described herein can be used to stimulate, such as the conversion of vellus hair to growth as terminal hair, as well as increasing the rate of growth of terminal hair. The utility of the compounds described herein for the simulation of hair growth was discovered as follows.

In the course of treating patients having glaucoma, treatment may only be appropriate in one eye. Within the course of daily practice, it was discovered that a patient who had been treated with bimatoprost, a prostaglandin analogue, developed lashed that were longer, thicker, and fuller in the treated eye than in the non-treated eye. On examination, the difference was found to be very striking. The lashes were longer and had a fuller, denser appearance in the treated eye. The lash appearance on the lids of the treated eyes would have appeared quite attractive if it represented a bilateral phenomenon. As a result of its asymmetric nature, the long lashes on one side could be construed as disturbing from a cosmetic standpoint. A systemic examination was preformed as a result of the asymmetric phenomenon. It soon became apparent that this altered appearance was not an isolated finding. Comparison of the lids of patients who were taking bimatoprost in only one eye revealed subtle changes in the lashed and adjacent hairs of the bimatoprost-treated side in several patients. Definite differences could be identified to varying degrees in the lashes and adjacent hairs of all patients who were taking the drug on a unilateral basis for longer than 6 months.

The changes in the lashes were apparent on gross inspection in several patients once attention was focused on the issue. In those with light colored hair and lashes, the differences were only seen easily with the aid of the high magnification and lighting capabilities of the slit lamp biomicroscope. In the course of glaucoma follow-up examination, attention is generally immediately focused on the eye itself. As a result of the high power magnification needed only one eye is seen at a time and the eye is seen at a high enough power that the lashes are not in focus. At these higher powers, any lash asymmetry between the two eyes is not likely to be noticed except by careful systematic comparison of the lashes and adjacent hairs of the eyelids of the two eyes.

Observed parameters leading to the conclusion that more robust hair growth occurred in the treatment area following administration of the prostaglandin analogue were multiple. They included increased length of lashed, increased number of lashes along the normal lash line, increased thickness and luster of lashes, increased auxiliary lash-like terminal hair in transitional areas adjacent to areas of normal lash growth, increased auxiliary lash-like terminal hairs at the medial and lateral canthal area, increased pigmentation of the lashes, increased numbers, increased length, as well as increased luster, and thickness of fine hair on the skin of the adjacent lid, and finally, increased perpendicular angulation of lashes and lash-like terminal hairs. The conclusion that hair growth is stimulated by prostaglandin analogues such as bimatoprost is thus supported not by evidence of a difference in a single parameter, but is based on multiple parameters of hair appearance in treated versus control areas in many subjects.

The compounds described herein are prostaglandin analogues and therefore have similar activities as bimatoprost, contain structural similarities, and therefore are expected to stimulate hair growth and stimulation of the conversion of vellus hair to terminal hair. In one embodiment, the compounds described herein and their prodrugs can be used for the stimulation of hair growth. As used herein, hair growth includes hair associated with the scalp, eyebrows, eyelids, beard, and other areas of the skin of animals.

In one embodiment, the compound is mixed with a dermatologically compatible vehicle or carrier. The vehicle, which may be employed for preparing compositions as described herein, may comprise, for example, aqueous solutions such as e.g., physiological salines, oil solutions, or ointments. The vehicle furthermore may contain dermatologically compatible preservatives such as e.g., benzalkonium chloride, surfactants like e.g., polysorbate 80, liposomes or polymers, for example, methyl cellulose, polyvinyl alcohol, polyvinyl pyrrolidone and hyaluronic acid; these may be used for increasing the viscosity. Furthermore, it is also possible to use soluble or insoluble drug inserts when the drug is to be administered.

In one embodiment, dermatological compositions can be formulated for topical treatment for the stimulation of hair growth which comprises an effective hair growth simulating amount of one or more compounds as defined above and a dermatologically compatible carrier. Effective amounts of the active compounds may be determined by one of ordinary skill in the art, but will vary depending on the compound employed, frequency of application and desired result. The compound will generally range from about 0.0000001 to about 50% by weight of the dermatological composition. Preferably, the compound will range from about 0.001 to about 50% by weight of total dermatological composition, more preferably from about 0.1 to about 30% by weight of the composition.

In one embodiment, the application of the present compounds for stimulation of hair growth finds applications in mammalian species, including both humans and animals. In humans, the compounds described herein can be applied for example, to the scalp, face beard, head, pubic area, upper lip, eyebrows, and eyelids. In animal raised for their pelts, e.g., mink, the compounds described herein can be applied over the entire surface of the body to improve the overall pelt for commercial reasons. The process can also be used for cosmetic reasons in animals, e.g., applied to the skin of dogs and cats having bald patches due to mange or other diseases causing a degree of alopecia.

The pharmaceutical compositions contemplated for the stimulation of hair growth include pharmaceutical compositions suited for topical and local action. The term "topical" as employed herein relates to the use of a compound, as described herein, incorporated in a suitable pharmaceutical carrier, and applied at the site of thinning hair or baldness for exertion of local action. Accordingly, such topical compositions include those pharmaceutical forms in which the compound is applied externally by direct contact with the skin to be treated. Conventional pharmaceutical forms for this purpose include ointments, liniments, creams, shampoos, lotions, pastes, jellies, sprays, aerosols, and the like, and may be applied in patches or impregnated dressings depending on the part of the body to be treated. The term "ointment" embraces formulations (including creams) having oleaginous, water-soluble and emulsion-type bases, e.g., petrolatum, lanolin, polyethylene glycols, as well as mixtures of these.

Typically, the compounds can be applied repeatedly for the sustained period of time topically on the part of the body to be treated, for example, the eyelids, eyebrows, skin or scalp. The preferred dosage regimen will generally involve regular, such as daily, administration for a period of treatment of at least one month, more preferably at least three months, and most preferably, at least six months.

For topical use on the eyelids or eyebrows, the active compounds can be formulated in aqueous solutions, creams, ointments, or oils exhibiting physologicla acceptable osmolarity by addition of pharmaceutically acceptable buffers and salts, such formulations may or may not, depending on the dispenser, contain preservatives such as benzalkonium chloride, chlorhexidine, chlorobutanol, parahydroxybenzoic acids and phenylmercuric salts such as nitrate, chloride, acetate, and borate, or antioxidants, as well as additives like EDTA, sorbitol, boric acid and the like as additives. Furthermore, particularly aqueous solutions may contain viscosity increasing agents such as polysaccharides, e.g., methylcellulose, mucopolysaccharides, e.g., hyaluronic acid and chondroitin sulfate, or poly alcohol, e.g., polyvinylalcohol. Various slow releasing gels and matrices may also be employed as well as soluble and insoluble ocular inserts, for instance, based on substances forming in situ gels. Depending on the actual formation and compound to be used, various amounts of the drug and different dose regimens may be employed. Typically, the daily amount of compound for treatment of the eyelid may be about 0.1 ng to about 100 mg per eyelid.

For topical use on the skin and scalp, the compound can be advantageously formulated using ointments, creams, liniments or patches as a carrier of the active ingredient. Also, these formulations may or may not contain preservatives, depending on the dispenser and nature of use. Such preservatives include those mentioned above, and methyl-, propyl-, or butyl-parahydroxybenzoic acid, betain, chlorhexidine, benzalkonium chloride, and the like. Various matrices for the slow release delivery may also be used. Typically, the dose to be applied on the scalp is in the range of about 0.1 ng to about 100 mg per day, more preferably about 1 ng to about 10 mg per day, and most preferably about 10 ng to about 1 mg per day depending on the compound and the formulation. To achieve the daily amount of medication depending on the formulation, the compound may be administered once or several times daily with or without antioxidants.

For topical use, creams, ointments, gels, solutions or suspensions, etc., containing the compound disclosed herein are employed. Topical formulations may generally be comprised of a pharmaceutical carrier, cosolvent, emulsifier, penetration enhancer, preservative system, and emollient.

The actual dose of the active compounds of the present invention depends on the specific compound, and on the condition to be treated; the selection of the appropriate dose is well within the knowledge of the skilled artisan.

The compounds disclosed herein are also useful in combination with other drugs useful for the treatment of glaucoma or other conditions.

For the treatment of glaucoma, combination treatment with the following classes of drugs are contemplated:

β-Blockers (or β-adrenergic antagonists) including carteolol, levobunolol, metiparanolol, timolol hemihydrate, timolol maleate, $\beta 1$-selective antagonists such as betaxolol, and the like, or pharmaceutically acceptable salts or prodrugs thereof;

Adrenergic Agonists including non-selective adrenergic agonists such as epinephrine borate, epinephrine hydrochloride, and dipivefrin, and the like, or pharmaceutically acceptable salts or prodrugs thereof; and $\alpha_2$-selective adrenergic agonists such as apraclonidine, brimonidine, and the like, or pharmaceutically acceptable salts or prodrugs thereof;

Carbonic Anhydrase Inhibitors including acetazolamide, dichlorphenamide, methazolamide, brinzolamide, dorzolamide, and the like, or pharmaceutically acceptable salts or prodrugs thereof;

Cholinergic Agonists including direct acting cholinergic agonists such as carbachol, pilocarpine hydrochloride, pilocarbine nitrate, pilocarpine, and the like, or pharmaceutically acceptable salts or prodrugs thereof;

cholinesterase inhibitors such as demecarium, echothiophate, physostigmine, and the like, or pharmaceutically acceptable salts or prodrugs thereof;

Glutamate Antagonists and other neuroprotective agents such as $Ca^{2+}$ channel blockers such as memantine, amantadine, rimantadine, nitroglycerin, dextrophan, detromethorphan, CGS-19755, dihydropyridines, verapamil, emopamil, benzothiazepines, bepridil, diphenylbutylpiperidines, diphenylpiperazines, HOE 166 and related drugs, fluspirilene, eliprodil, ifenprodil, CP-101,606, tibalosine, 2309BT, and 840S, flunarizine, nicardipine, nifedimpine, nimodipine, barnidipine, verapamil, lidoflazine, prenylamine lactate, amiloride, and the like, or pharmaceutically acceptable salts or prodrugs thereof;

Prostamides such as bimatoprost, or pharmaceutically acceptable salts or prodrugs thereof; and Prostaglandins including travoprost, UFO-21, chloprostenol, fluprostenol, 13,14-dihydro-chloprostenol, isopropyl unoprostone, latanoprost and the like.

Cannabinoids including CB1 agonists such as WIN-55212-2 and CP-55940 and the like, or pharmaceutically acceptable salts or prodrugs thereof.

For treatment of diseases affecting the eye including glaucoma, these compounds can be administered topically, periocularly, intraocularly, or by any other effective means known in the art.

In addition to the treatment of glaucoma, prostaglandin $EP_2$ selective agonists are believed to have several medical uses. For example, U.S. Pat. No. 6,437,146 teaches the use of prostaglandin $EP_2$ selective agonists "for treating or preventing inflammation and pain in joint and muscle (e.g., rheumatoid arthritis, rheumatoid spondylitis, osteoarthritis, gouty arthritis, juvenile arthritis, etc.), inflammatory skin condition (e.g., sunburn, burns, eczema, dermatitis, etc.), inflammatory eye condition (e.g., conjunctivitis, etc.), lung disorder in which inflammation is involved (e.g., asthma, bronchitis, pigeon fancier's disease, farmer's lung, etc.), condition of the gastrointestinal tract associated with inflammation (e.g., aphthous ulcer, Chrohn's disease, atrophic gastritis, gastritis varialoforme, ulcerative colitis, coeliac disease, regional ileitis, irritable bowel syndrome, etc.), gingivitis, inflammation, pain and tumescence after operation or injury, pyrexia, pain and other conditions associated with inflammation, allergic disease, systemic lupus crythematosus, scleroderma, polymyositis, tendinitis, bursitis, periarteritis nodose, rheumatic fever, Sjgren's syndrome, Behcet disease, thyroiditis, type I diabetes, diabetic complication (diabetic microangiopathy, diabetic retinopathy, diabetic neohropathy, etc.), nephrotic syndrome, aplastic anemia, myasthenia gravis, uveitis contact dermatitis, psoriasis, Kawasaki disease, sarcoidosis, Hodgkin's disease, Alzheimers disease, kidney dysfunction (nephritis, nephritic syndrome, etc.), liver dysfunction (hepatitis, cirrhosis, etc.), gastrointestinal dysfunction (diarrhea, inflammatory bowel disease, etc.) shock, bone disease characterized by abnormal bone metabolism such as osteoporosis (especially, postmenopausal osteoporosis), hypercalcemia, hyperparathyroidism, Paget's bone diseases, osteolysis, hypercalcemia of malignancy with or without bone metastases, rheumatoid arthritis, periodonritis, osteoarthritis, ostealgia, osteopenia, cancer cachexia, calculosis, lithiasis (especially, urolithiasis), solid carcinoma, mesangial proliferative glomerulonephritis, edema (e.g. cardiac edema, cerebral edema, etc.), hypertension such as malignant hypertension or the like, premenstrual tension, urinary calculus, oliguria such as the one caused by acute or chronic failure, hyperphosphaturia, or the like."

U.S. Pat. No 6,710,072 teaches the use of EP2 agonists for the treatment or prevention of "osteoporosis, constipation, renal disorders, sexual dysfunction, baldness, diabetes, cancer and in disorder of immune regulation . . . various pathophysiological diseases including acute myocardial infarction, vascular thrombosis, hypertension, pulmonary hypertension, ischemic heart disease, congestive heart failure, and angina pectoris."

These compounds can also be used to treat or prevent conditions affecting the posterior part of the eye include maculopathies/retinal degeneration such as non-exudative age related macular degeneration (ARMD), exudative age related macular degeneration (ARMD), choroidal neovascularization, diabetic retinopathy, acute macular neuroretinopathy, central serous chorioretinopathy, cystoid macular edema, and diabetic macular edema; uveitis/retinitis/choroiditis such as acute multifocal placoid pigment epitheliopathy, Behcet's disease, birdshot retinochoroidopathy, infectious (syphilis, lyme, tuberculosis, toxoplasmosis), intermediate uveitis (pars planitis), multifocal choroiditis, multiple evanescent white dot syndrome (mewds), ocular sarcoidosis, posterior scleritis, serpiginous choroiditis, subretinal fibrosis and uveitis syndrome, Vogt-Koyanagi-and Harada syndrome; vasuclar diseases/exudative diseases such as retinal arterial occlusive disease, central retinal vein occlusion, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angiitis, sickle cell retinopathy and other hemoglobinopathies, angioid streaks, familial exudative vitreoretinopathy, and Eales disease; traumatic/surgical conditions such as sympathetic ophthalmia, uveitic retinal disease, retinal detachment, trauma, conditions caused by laser, conditions caused by photodynamic therapy, photocoagulation, hypoperfusion during surgery, radiation retinopathy, and bone marrow transplant retinopathy; proliferative disorders such as proliferative vitreal retinopathy and epiretinal membranes, and proliferative diabetic retinopathy; infectious disorders such as ocular histoplasmosis, ocular toxocariasis, presumed ocular histoplasmosis syndrome (POHS), endophthalmitis, toxoplasmosis, retinal diseases associated with HIV infection, choroidal disease associate with HIV infection, uveitic disease associate with HIV infection, viral retinitis, acute retinal necrosis, progressive outer retinal necrosis, fungal retinal diseases, ocular syphilis, ocular tuberculosis, diffuse unilateral subacute neuroretinitis, and myiasis; genetic disorders such as retinitis pigmentosa, systemic disorders with accosiated retinal dystrophies, congenital stationary night blindness, cone dystrophies, Stargardt's disease and fundus flavimaculatus, Best's disease, pattern dystrophy of the retinal pigmented epithelium, X-linked retinoschisis, Sorsby's fundus dystrophy, benign concentric maculopathy, Bietti's crystalline dystrophy, and pseudoxanthoma elasticum; retinal tears/holes such as retinal detachment, macular hole, and giant retinal tear; tumors such as retinal disease associated with tumors, congenital hypertrophy of the retinal pigmented epithelium, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, and intraocular lymphoid tumors; and miscellaneous other diseases affecting the posterior part of the eye such as punctate inner choroidopathy, acute posterior multifocal placoid pigment epitheliopathy, myopic retinal degeneration, and acute retinal pigement epitheliitis. Preferably, the disease or condition is retinitis pigmentosa, proliferative vitreal retinopathy (PVR), age-related macular degeneration (ARMD), diabetic retinopathy, diabetic macular edema, retinal detachment, retinal tear, uveitus, or cytomegalovirus retinitis.

These compounds are also useful in treating asthma.

Synthetic Methods

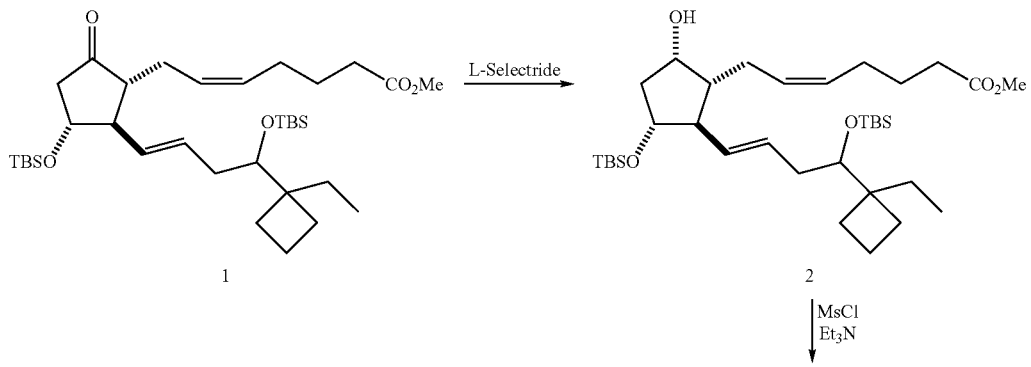

-continued

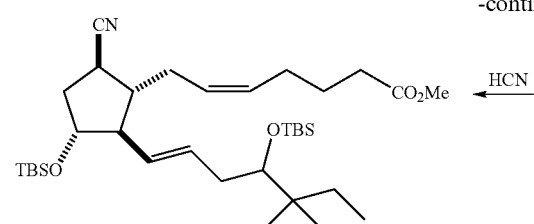
4

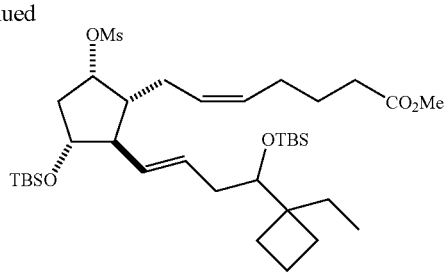
3

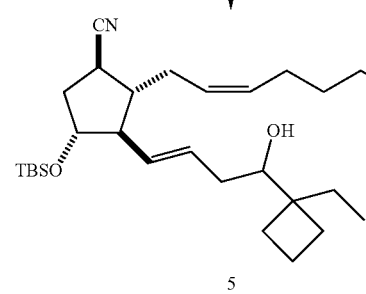
5

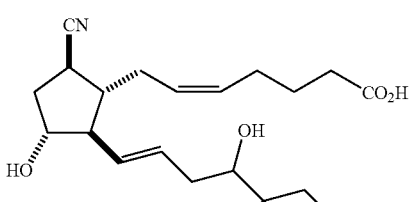
6H

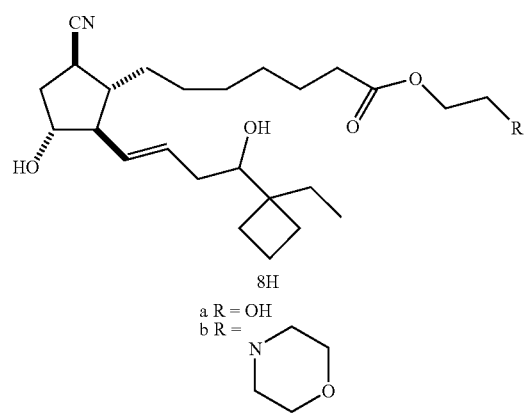
8H
a R = OH
b R =

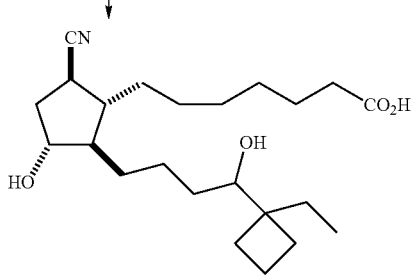
7H

EXAMPLE 1

(Z)-methyl 7-((1R,2R,3R)-3-(tert-butyidimethylsilyloxy)-2-((E)-4-(tert-butyidimethylsilyloxy)-4-(1-ethylcyclobutyl)but-1-enyl)-5-oxocyclopentyl)hept-5-enoate For the preparation of Methyl Ester (1), see Kousuke, T. et al. *Bioorg. Med. Chem.* 2002, 10, 1093.

EXAMPLE 2

(Z)-methyl 7-((1R,2R,3R,5S)-3-(tert-butyidimethyl-silyloxy)-2-((E)-4-(tert-butyldimethylsilyloxy)-4-(1-ethylcyclobutyl)but-1-enyl)-5-hydroxycyclopentyl) hept-5-enoate L-Selectride (1.2 mL, 1.2 mmol; 1 M THF) was added to a solution of Ester (1) (540 mg, 0.869 mmol) in THF (15 mL) @ −78° C. After having stirred 30 min at this temperature, 3% $H_2O_2$ (27 mL) was added slowly and the reaction was warmed to room temperature and allowed to stir 60 min. $NH_4Cl$ (sat.) was added, and the mixture was extracted with EtOAc (3×). The combined organics were washed with brine, dried ($Na_2SO_4$) and concentrated. Flash Column Chromatography (FCC) 19:1 to 8:1 hexanes/EtOAc, gave 447 mg of Alcohol (2).

EXAMPLE 3

(Z)-methyl 7-((1R,2R,3R,5S)-3-(tert-butyidimethyl-silyloxy)-2-((E)-4-(tert-butyidimethylsilyloxy)-4-(1-ethylcyclobutyl)but-1-enyl)-5-(methylsulfonyloxy) cyclopentyl)hept-5-enoate MsCl (0.135 mL, 1.72 mmol) was added to a mixture of Alcohol (2) (447 mg, 0.717 mmol) and $Et_3N$ (217 mg, 2.15 mmol) in $CH_2Cl_2$ (5 mL) at rt. After 16 h, the mixture was quenched with $NaHCO_3$, extracted with $CH_2Cl_2$ (2×) and hexanes (1×). The combined organics were washed with brine, dried ($Na_2SO_4$), and concentrated. FCC 8:1 to 5:1 hexanes/EtOAc gave 372 mg of Mesylate (3).

EXAMPLE 4

(Z)-methyl 7-((1S,2R,3R,5R)-3-(tert-butyldimethyl-silyloxy)-2-((E)-4-(tert-butyldimethylsilyloxy)-4-(1-ethylcyclobutyl)but-1-enyl)-5-cyanocyclopentyl)hept-5-enoate KCN (105 mg, 1.62 mmol) was added to a solution of Mesylate (3) (372 mg, 0.54 mmol) in DMSO (6 mL), and the reaction was heated to 65° C. for 16 h. The mixture was diluted with water and brine, extracted with CHCl$_3$ (5×) and the combined organics were washed with water, dried (Na$_2$SO$_4$), and concentrated. FCC 9.5:0.5 hexanes/EtOAc gave 68 mg of Nitrile (4).

EXAMPLE 5

(Z)-methyl 7-((1S,2R,3R,5R)-5-cyano-2-((E)-4-(1-ethylcyclobutyl)-4-hydroxybut-1-enyl)-3-hydroxycyclopentyl)hept-5-enoate HF pyr (0.3 mL) was added to a solution of Nitrile (4) in MeCN (2 mL). After 3 h, the mixture was quenched with NaHCO$_3$, extracted with EtOAc (3×), and the combined organics were washed with brine, dried (Na$_2$SO$_4$), and concentrated. FCC 2:1 to 1:1 to 2:3 hexanes/EtOAc gave 8 mg of Diol (5) as a mixture of two diastereomers.

EXAMPLE 6H (Z)-7-((1S,2R,3R,5R)-5-cyano-2-((E)-4-(1-ethylcyclobutyl)-4-hydroxybut-1-enyl)-3-hydroxycyclopentyl)hept-5-enoic acid To the faster moving isomer of Diol (5) (4 mg, 0.0099 mmol) in THF (1 mL) was added a solution of 0.5 N LiOH (1 mL). After 16 h, the mixture was purified by FCC 100% EtOAc to give 1.2 mg of Acid (6H).

EXAMPLE 6L (Z)-7-((1S,2R,3R,5R)-5-cyano-2-((E)-4-(1-ethylcyclobutyl)-4-hydroxybut-1-enyl)-3-hydroxycyclopentyl)hept-5-enoic acid The slower moving diastereomer of Example 5 was reacted in accordance with the process of Example 6H to yield the above named compound.

EXAMPLE 7H 7-((1S,2R,3R,5R)-5-cyano-2-(4-(1-ethylcyclobutyl)-4-hydroxybutyl)-3-hydroxycyclopentyl)heptanoic acid Pd—C (4 mg) was added to a solution of Acid (6H) (4 mg, 0.01 mmol) in MeOH (2 mL) and the reaction was stirred under an atmosphere of H$_2$ for 16 h. The mixture was concentrated and FCC 100% EtOAc to 9:1 EtOAc/MeOH provided 3.1 mg of Acid (7H).

EXAMPLE 7L 7-((1S,2R,3R,5R)-5-cyano-2-(4-(1-ethylcyclobutyl)-4-hydroxybutyl)-3-hydroxycyclopentyl)heptanoic acid The compound obtained via Example 6L was reacted in accordance with the process of Example 7H to yield the above named compound.

EXAMPLE 8Ha

Triethylamine and ethyl chloroformate are added sequentially to a solution of compound 7H in CH$_2$Cl$_2$ at room temperature. After 2.5 h, triethylamine and ethylene glycol are added. After stirring overnight at room temperature, the reaction mixture is partitioned between H$_2$O and CH$_2$Cl$_2$. The phases are separated and the aqueous phase is extracted with CH$_2$Cl$_2$ (2×). The combined organic phase is washed with 1 N HCl then dried (MgSO$_4$), filtered and concentrated in vacuo. Purification of the residue by flash column chromatography on silica gel (10% CH$_3$OH/CH$_2$Cl$_2$) affords compound 8Ha.

EXAMPLE 8Hb

Triethylamine and ethyl chloroformate are added sequentially to a solution of compound 7H in CH$_2$Cl$_2$ at room temperature. After 2.5 h, triethylamine and 4-(2-hydroxyethyl)-morphine are added. After stirring overnight at room temperature, the reaction mixture is partitioned between H$_2$O and CH$_2$Cl$_2$. The phases are separated and the aqueous phase is extracted with CH$_2$Cl$_2$ (2×). The combined organic phase is washed with 1 N HCl then dried (MgSO$_4$), filtered and concentrated in vacuo. Purification of the residue by flash column chromatography on silica gel (10% CH$_3$OH/CH$_2$Cl$_2$) affords compound 8Hb.

EXAMPLE 8La

Triethylamine and ethyl chloroformate are added sequentially to a solution of compound 7L in CH$_2$Cl$_2$ at room temperature. After 2.5 h, triethylamine and ethylene glycol are added. After stirring overnight at room temperature, the reaction mixture is partitioned between H$_2$O and CH$_2$Cl$_2$. The phases are separated and the aqueous phase is extracted with CH$_2$Cl$_2$ (2×). The combined organic phase is washed with 1 N HCl then dried (MgSO$_4$), filtered and concentrated in vacuo. Purification of the residue by flash column chromatography on silica gel (10% CH$_3$OH/CH$_2$Cl$_2$) affords compound 8La.

EXAMPLE 8Hb

Triethylamine and ethyl chloroformate are added sequentially to a solution of compound 7H in CH$_2$Cl$_2$ at room temperature. After 2.5 h, triethylamine and 4-(2-hydroxyethyl)-morphine are added. After stirring overnight at room temperature, the reaction mixture is partitioned between H$_2$O and CH$_2$Cl$_2$. The phases are separated and the aqueous phase is extracted with CH$_2$Cl$_2$ (2×). The combined organic phase is washed with 1 N HCl then dried (MgSO$_4$), filtered and concentrated in vacuo. Purification of the residue by flash column chromatography on silica gel (10% CH$_3$OH/CH$_2$Cl$_2$) affords compound 8Hb.

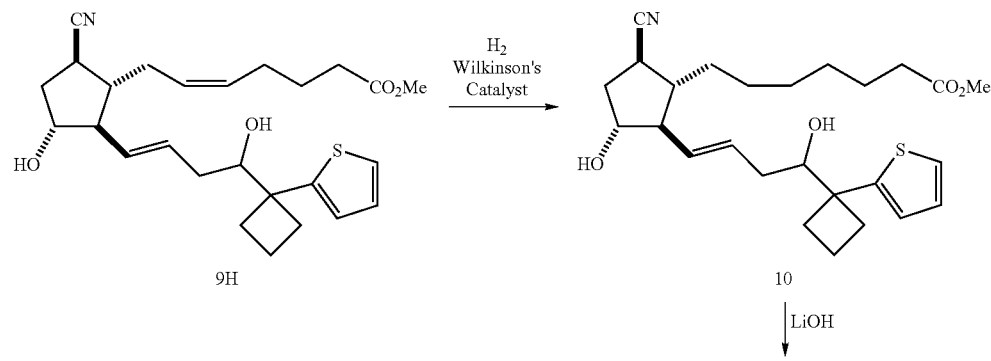
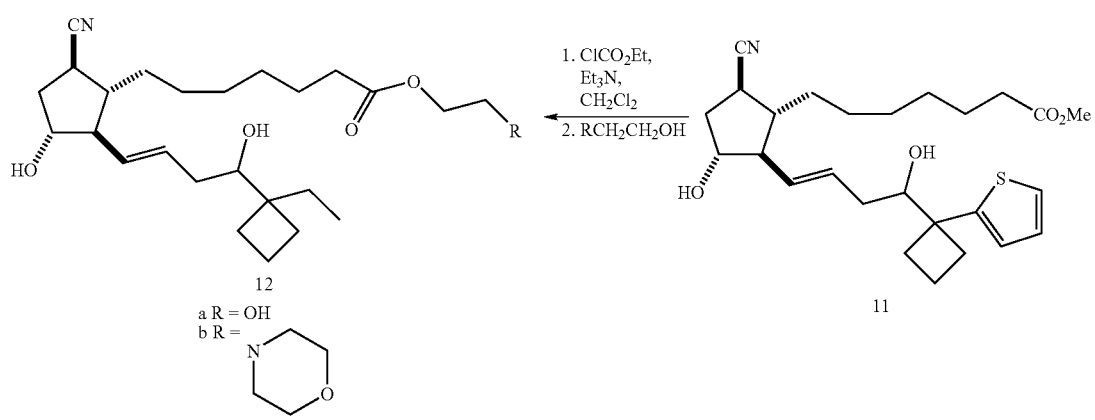
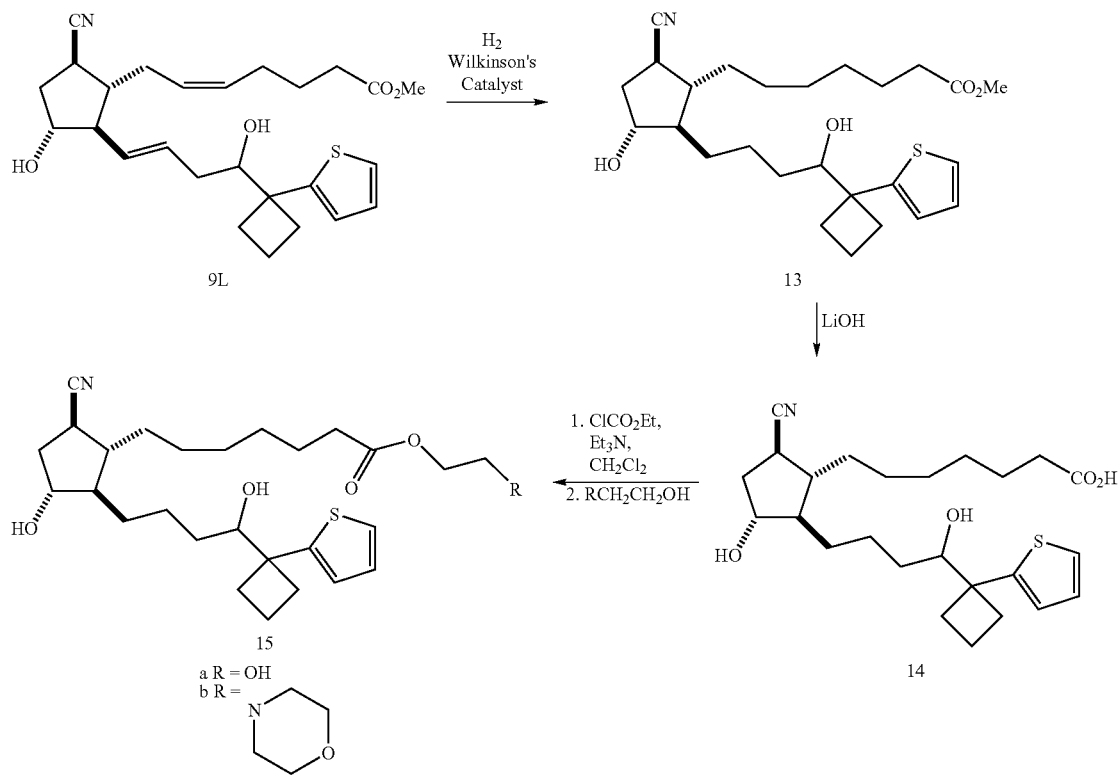

EXAMPLE 9H (Z)-methyl 7-((1S,2R,3R,5R)-5-cyano-3-hydroxy-2-((E)-4-hydroxy-4-(1-(thiophen-2-yl)cyclobutyl)but-1-enyl)cyclopentyl)hept-5-enoate

EXAMPLE 9L (Z)-methyl 7-((1S,2R,3R,5R)-5-cyano-3-hydroxy-2-((E)-4-hydroxy-4-(1-(thiophen-2-yl)cyclobutyl)but-1-enyl)cyclopentyl)hept-5-enoate

EXAMPLE 10 methyl 7-((1S,2R,3R,5R)-5-cyano-3-hydroxy-2-((E)-4-hydroxy-4-(1-(thiophen-2-yl)cyclobutyl)but-1-enyl)cyclopentyl)heptanoate Wilkinson's Catalyst (5 mg, 0.0055 mmol) was added to a solution of Ester (9H) in EtOH(5 mL). The reaction stirred under an atmosphere of $H_2$ for 16 h, was concentrated, and FCC 1:1 hexanes/EtOAc provided 2.6 mg of Ester (10).

EXAMPLE 11

7-((1S,2R,3R,5R)-5-cyano-3-hydroxy-2-((E)-4-hydroxy-4-(1-(thiophen-2-yl)cyclobutyl)but-1-enyl)cyclopentyl)heptanoic acid The compound obtained via Example 10 was reacted in accordance with the process of Example 6H to yield the above named compound.

EXAMPLE 12a

Triethylamine and ethyl chloroformate are added sequentially to a solution of compound 11 in $CH_2Cl_2$ at room temperature. After 2.5 h, triethylamine and ethylene glycol are added. After stirring overnight at room temperature, the reaction mixture is partitioned between $H_2O$ and $CH_2Cl_2$. The phases are separated and the aqueous phase is extracted with $CH_2Cl_2$ (2×). The combined organic phase is washed with 1 N HCl then dried ($MgSO_4$), filtered and concentrated in vacuo. Purification of the residue by flash column chromatography on silica gel (10% $CH_3OH/CH_2Cl_2$) affords compound 12a.

EXAMPLE 12b

Triethylamine and ethyl chloroformate are added sequentially to a solution of compound 11 in $CH_2Cl_2$ at room temperature. After 2.5 h, triethylamine and 4-(2-hydroxyethyl)-morphine are added. After stirring overnight at room temperature, the reaction mixture is partitioned between $H_2O$ and $CH_2Cl_2$. The phases are separated and the aqueous phase is extracted with $CH_2Cl_2$ (2×). The combined organic phase is washed with 1 N HCl then dried ($MgSO_4$), filtered and concentrated in vacuo Purification of the residue by flash column chromatography on silica gel (10% $CH_3OH/CH_2Cl_2$) affords compound 12b.

EXAMPLE 13 methyl 7-((1,2R,3R,5R)-5-cyano-3-hydroxy-2-(4-hydroxy-4-(1-(thiophen-2-yl)cyclobutyl)butyl)cyclopentyl)heptanoate Wilkinson's Catalyst (5 mg, 0.0055 mmol) was added to a solution of Ester (9L) in EtOH(5 mL). The reaction stirred under an atmosphere of $H_2$ for 16 h, was concentrated, and FCC 1:1 hexanes/EtOAc provided 2.6 mg of Ester (13).

EXAMPLE 14

7-((1S,2R,3R,5R)-5-cyano-3-hydroxy-2-(4-hydroxy-4-(1-(thiophen-2-yl)cyclobutyl)butyl)cyclopentyl)heptanoic acid The compound obtained via Example 13 was reacted in accordance with the process of Example 6H to yield the above named compound.

EXAMPLE 15a

The compound obtained via Example 14 was reacted in accordance with the process of Example 12a to yield the compound 15a.

EXAMPLE 15b

The compound obtained via Example 14 was reacted in accordance with the process of Example 12b to yield compound 15b.

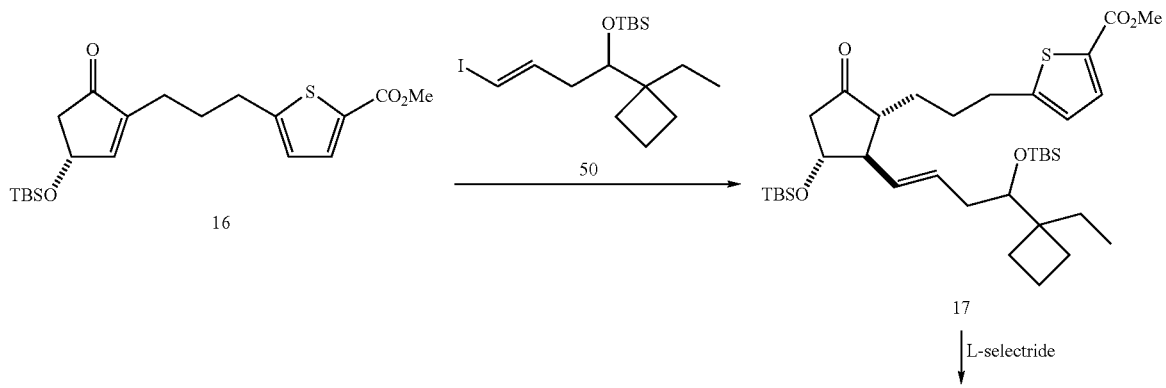

-continued
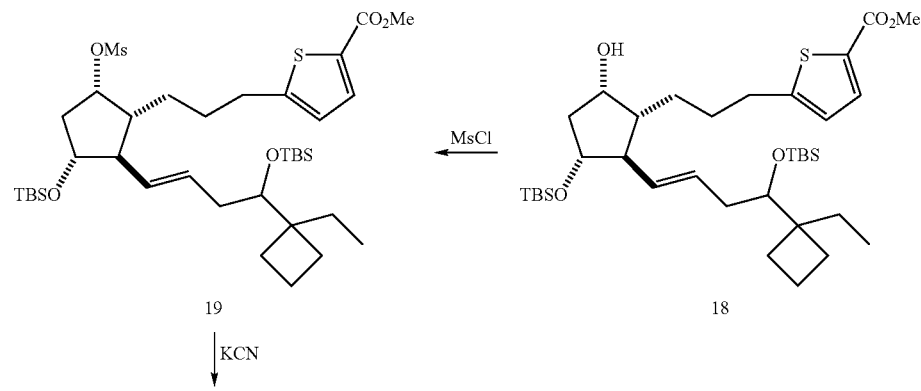
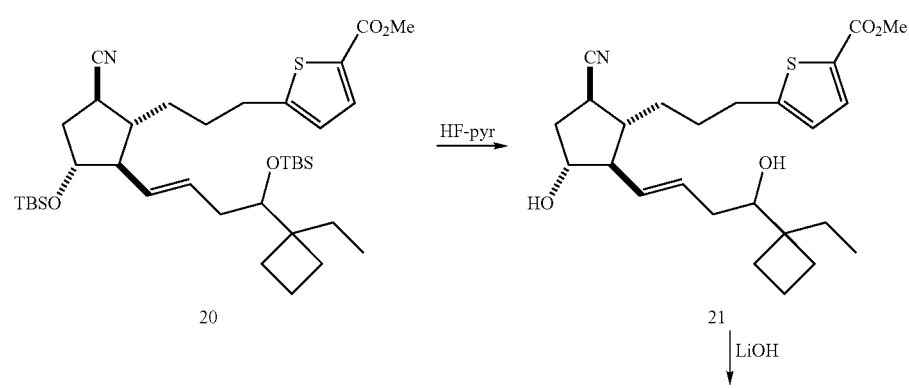
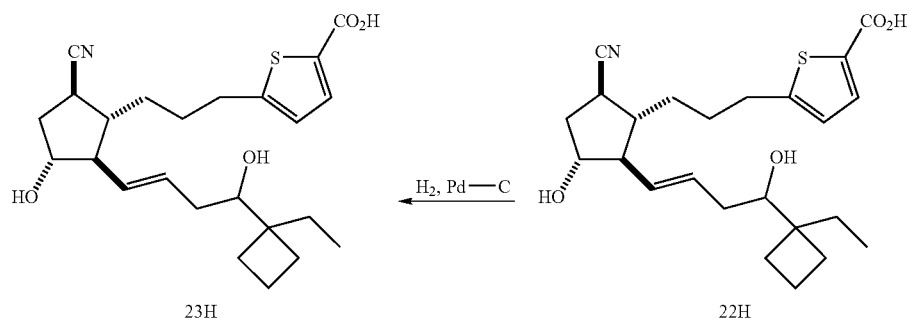

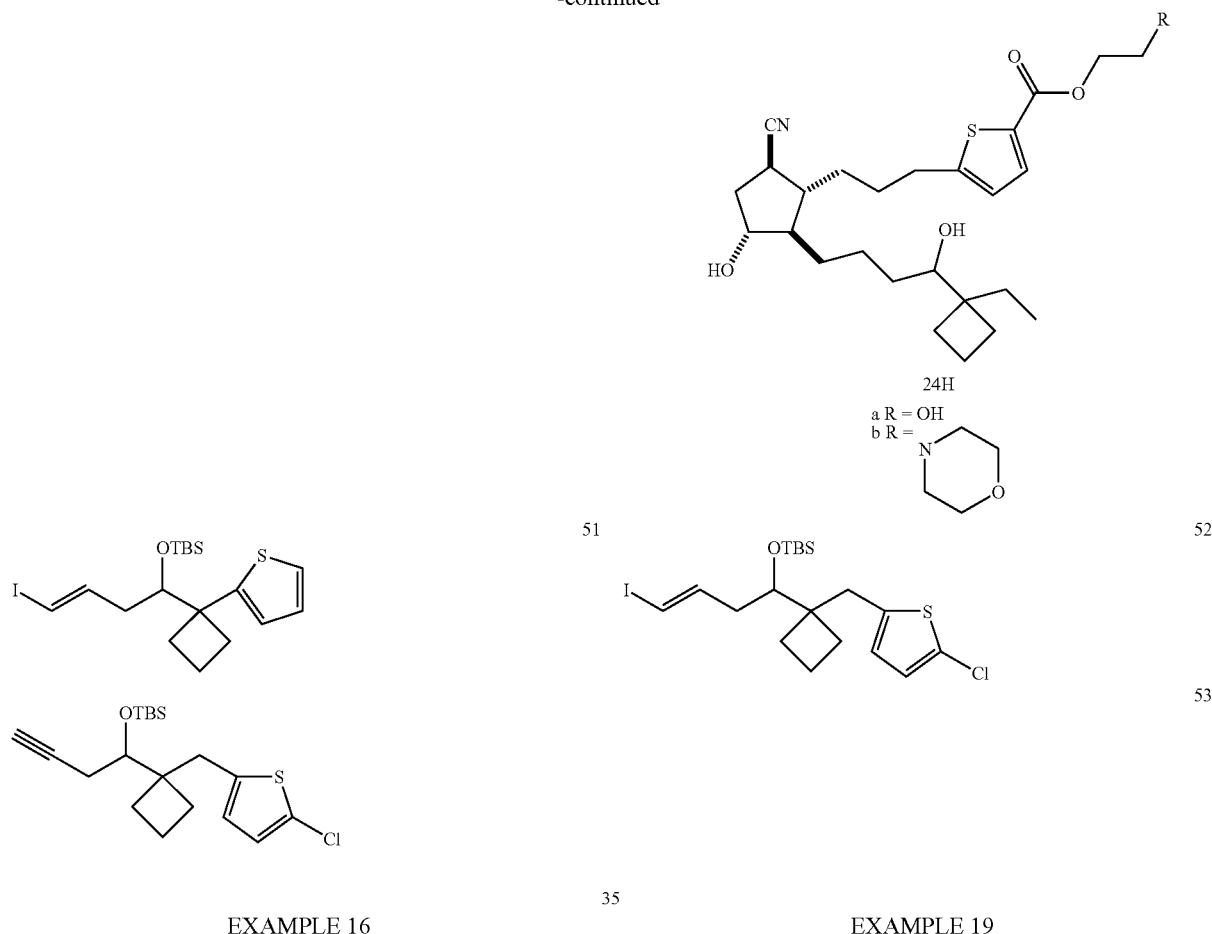

EXAMPLE 16

(R)-methyl 5-(3-(3-(tert-butyidimethylsilyloxy)-5-oxocyclopent-1-enyl)propyl)thiophene-2-carboxylate This compound was prepared as described in U.S. Provisional Patent Application No. 60/744,236 filed on Apr. 4, 2006, which is incorporated by reference herein.

EXAMPLE 17 methyl 5-(3-((1R,2R,3R)-3-(tert-butyidimethylsilyloxy)-2-((E)-4-(tert-butyldimethylsilyloxy)-4-(1-ethylcyclobutyl)but-1-enyl)-5-oxocyclopentyl)propyl)thiophene-2-carboxylate The compound obtained via Example 16 was reacted in accordance with the process of Example 1 to yield the above named compound.

EXAMPLE 18 methyl 5-(3-((1R,2R,3R,5S)-3-(tert-butyidimethylsilyloxy)-2-((E)-4-(tert-butyidimethylsilyloxy)-4-(1-ethylcyclobutyl)but-1-enyl)-5-hydroxycyclopentyl)propyl)thiophene-2-carboxylate The compound obtained via Example 17 was reacted in accordance with the process of Example 2 to yield the above named compound.

EXAMPLE 19 methyl 5-(3-((1R,2R,3R,5S)-3-(tert-butyldimethylsilyloxy)-2-((E)-4-(tert-butyldimethylsilyloxy)-4-(1-ethylcyclobutyl)but-1-enyl)-5-(methylsulfonyloxy)cyclopentyl)propyl)thiophene-2-carboxylate The compound obtained via Example 18 was reacted in accordance with the process of Example 3 to yield the above named compound.

EXAMPLE 20 methyl 5-(3-((1S,2R,3R,5R)-3-(tert-butyldimethylsilyloxy)-2-((E)-4-(tert-butyldimethylsilyloxy)-4-(1-ethylcyclobutyl)but-1-enyl)-5-cyanocyclopentyl)propyl)thiophene-2-carboxylate The compound obtained via Example 19 was reacted in accordance with the process of Example 4 to yield the above named compound.

EXAMPLE 21 methyl 5-(3-((1S,2R,3R,5R)-5-cyano-2-((E)-4-(1-ethylcyclobutyl)-4-hydroxybut-1-enyl)-3-hydroxycyclopentyl)propyl)thiophene-2-carboxylate The compound obtained via Example 20 was reacted in accordance with the process of Example 5 to yield the above named compound.

EXAMPLE 22H 5-(3-((1S,2R,3R,5R)-5-cyano-2-((E)-4-(1-ethylcyclobutyl)-4-hydroxybut-1-hydroxycyclopentyl)propyl)thiophene-2-carboxylic acid The faster moving isomer obtained via Example 21 was reacted in accordance with the process of Example 6H to yield the above named compound.

EXAMPLE 22L 5-(3-((1S,2R,3R,5R)-5-cyano-2-((E)-4-(1-ethylcyclobutyl)-4-hydroxybut-1-enyl)-3-hydroxycyclopentyl)propyl)thiophene-2-carboxylic acid The slower moving isomer obtained via Example 21 was reacted in accordance with the process of Example 6L to yield the above named compound.

EXAMPLE 23H 5-(3-((1S,2R,3R,5R)-5-cyano-2-(4-(1-ethylcyclobutyl)-4-hydroxybutyl)-3-hydroxycyclopentyl)propyl)thiophene-2-carboxylic acid The compound obtained via Example 22H was reacted in accordance with the process of Example 7H to yield the above named compound.

EXAMPLE 23L 5-(3-((1S,2R,3R,5R)-5-cyano-2-(4-(1-ethylcyclobutyl)-4-hydroxybutyl)-3-hydroxycyclopentyl)propyl)thiophene-2-carboxylic acid The compound obtained via Example 22L was reacted in accordance with the process of Example 7L to yield the above named compound.

EXAMPLE 24Ha

The compound obtained via Example 23H was reacted in accordance with the process of Example 8Ha to yield compound 24Ha.

EXAMPLE 24Hb

The compound obtained via Example 23H was reacted in accordance with the process of Example 8Hb to yield compound 24Hb.

EXAMPLE 24La

The compound obtained via Example 23L was reacted in accordance with the process of Example 8La to yield compound 24La.

EXAMPLE 24Lb

The compound obtained via Example 23L was reacted in accordance with the process of Example 8Lb to yield compound 24Lb.

EXAMPLE 50

(E)-tert-butyl(1-(1-ethylcyclobutyl)-4-iodobut-3-enyloxy)dimethylsilane

For the preparation of Vinyl Iodide, see Kousuke, T. et al. *Bioorg. Med. Chem.* 2002, 10, 1093.

EXAMPLE 51

(E)-tert-butyl(4-iodo-1-(1-(thiophen-2-yl)cyclobutyl)but-3-enyloxy)dimethylsilane The named compound was purchased from JSTAR RESEARCH, Inc., South Plainfield, N.J., 07080

EXAMPLE 52

(E)-tert-butyl(1-(1-((5-chlorothiophen-2-yl)methyl)cyclobutyl)-4-iodobut-3-enyloxy)dimethylsilane The compound obtained via Example 53 was reacted in accordance with the process of Example 50 to yield the above named compound.

EXAMPLE 53 tert-butyl(1-(1-((5-chlorothiophen-2-yl)methyl)cyclobutyl)but-3-ynyloxy)dimethylsilane The named compound was purchased from JSTAR RESEARCH, Inc., South Plainfield, N.J., 07080

Treatment of inflammatory bowel disease may be accomplished by the administration of the compounds described herein to the suffering mammal. Inflammatory bowel disease describes a variety of diseases characterized by inflammation of the bowels including, but not limited to, ulcerative colitis and Crohn's disease. Treatment may be accomplished by oral administration, by suppository, or parenteral administration, or some other suitable method.

While not intending to limit the scope of the invention in any way, delivery of the compounds disclosed herein to the colon via oral dosage forms may be accomplished by any of a number of methods known in the art. For example, reviews by Chourasia and Jain in J Pharm Pharmaceul Sci 6 (1): 33-66, 2003 and Shareef et. al (AAPS PharmSci 2003; 5 (2) Article 17) describe a number of useful methods. While not intending to limit the scope of the invention in any way these methods include 1) administration of a prodrug, including an azo or a carbohydrate based prodrug; 2) coating the drug with, or encapsulating or impregnating the drug into a polymer designed for delivery to the colon, 3) time released delivery of the drug, 4) use of a bioadhesive system; and the like.

While not intending to be bound in any way by theory, it is believed that intestinal microflora is capable of reductive cleavage of an azo bond leaving the two nitrogen atoms as amine functional groups. While not intending to limit the scope of the invention in any way, the azo prodrug approach has been used to deliver to 5-aminosalicylic acid to the colons of humans in clinical trials for the treatment of inflammatory bowel disease. It is also believed that bacteria of the lower GI also have enzymes which can digest glycosides, glucuronides, cyclodextrins, dextrans, and other carbohydrates, and ester prodrugs formed from these carbohydrates have been shown to deliver the parent active drugs selectively to the colon. For example, in vivo and in vitro studies on rats and guinea pigs with prodrugs of dexamethasone, prednisolone, hydrocortisone, and fludrocortisone, suggest that glycoside conjugates may be useful for the delivery of steroids to the human colon. Other in vivo studies have suggested that glucouronide, cyclodextrin, and dextran prodrugs of steroids or non-steroidal anti-inflammatory drugs are useful for delivery of these drugs to the lower GI tract. An amide of salicylic acid and glutamic acid has been shown to be useful for the delivery of salicylic acid to the colon of rabbit and dog.

While not intending to limit the scope of the invention in any way, carbohydrate polymers such as amylase, arabinogalactan, chitosan, chondroiton sulfate, dextran, guar gum, pectin, xylin, and the like, or azo-group containing polymers can be used to coat a drug compound, or a drug may be impregnated or encapsulated in the polymer. It is believed that after oral administration, the polymers remain stable in the upper GI tract, but are digested by the microflora of the lower GI thus releasing the drug for treatment.

Polymers which are sensitive to pH may also be used since the colon has a higher pH than the upper GI tract. Such polymers are commercially available. For example, Rohm Pharmaceuticals, Darmstadt, Germany, commercially provides pH dependent methacrylate based polymers and copolymers which have varying solubilities over different pH ranges based upon the number of free carboxylate groups in the polymer under the tradename Eudragit®. Several Eudragit® dosage forms are currently used to deliver saisalazine for the treatment of ulcerative colitis and Crohn's disease. Time release systems, bioadhesive systems, and other delivery systems have also been studied.

The following compounds are non-limiting examples of compounds useful according to present disclosure:

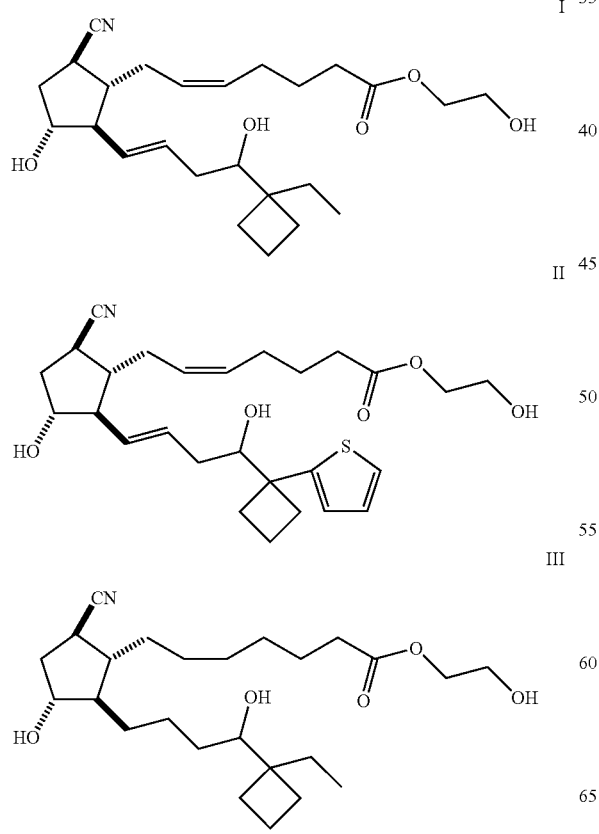

I

II

III

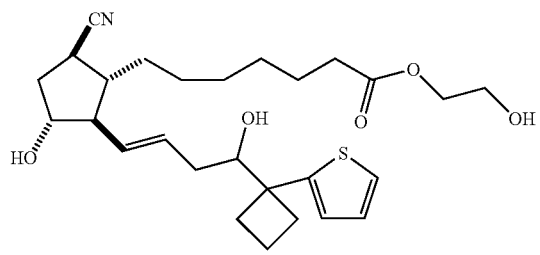

IV

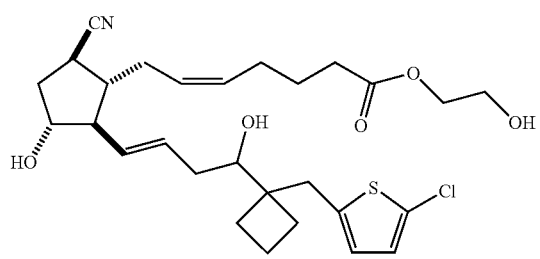

V

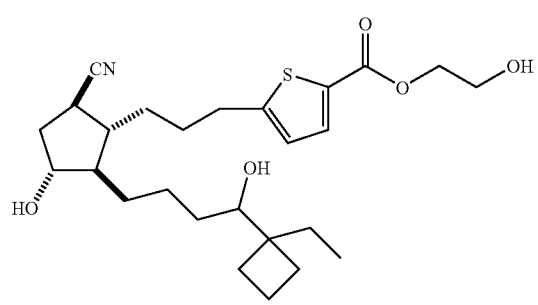

VI

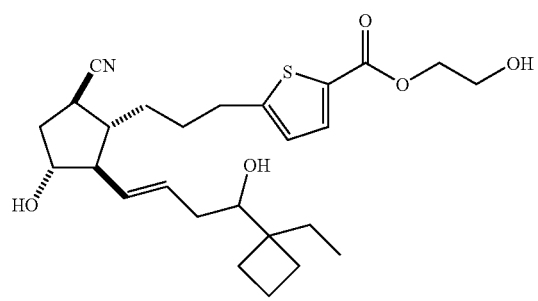

VII

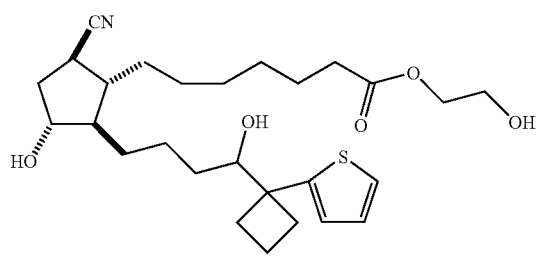

VIII

IX
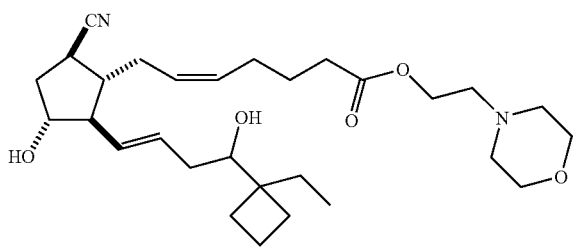

X
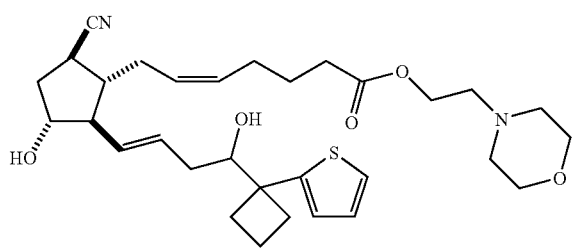

XI
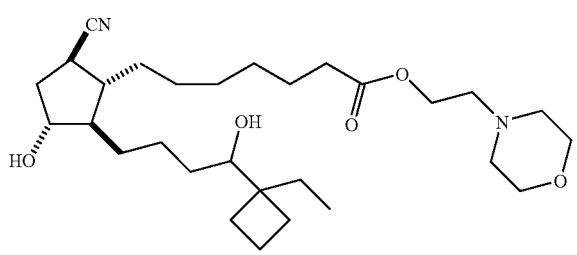

XII
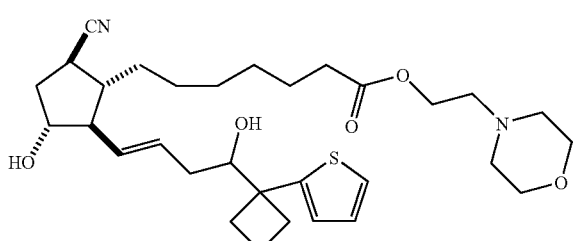

XIII
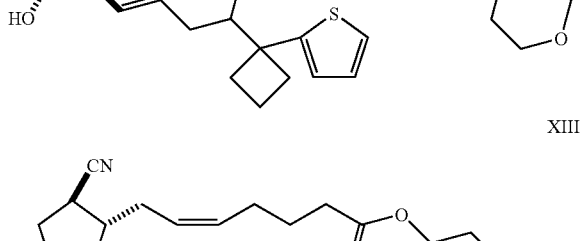

XIV
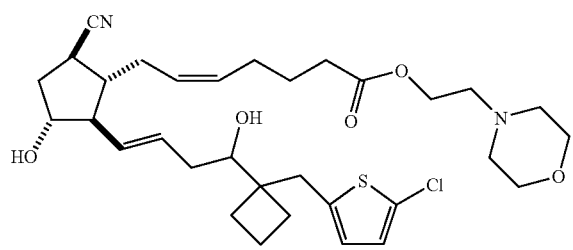

XV
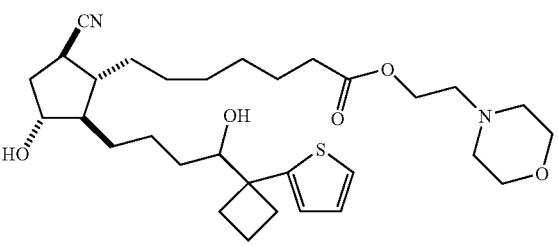

XVI
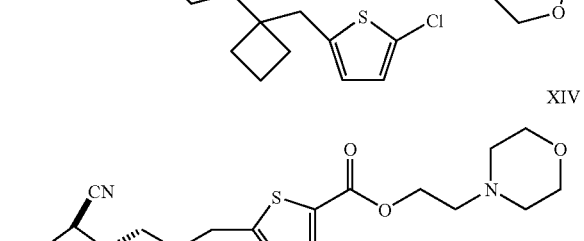

IN VIVO EXAMPLES

Compound I is tested in normotensive dogs. The intraocular pressure (IOP) decreases from baseline. This compound is also tested in laser-induced hypertensive monkeys, the IOP decreases from baseline.

Compound II is tested in normotensive dogs. The IOP decreases from baseline. This compound is also tested in laser-induced hypertensive monkeys, the IOP decreases from baseline.

Compound III is tested in normotensive dogs. The IOP decreases from baseline. This compound is also tested in laser-induced hypertensive monkeys, the IOP decreases from baseline.

Compound IV is tested in normotensive dogs. The IOP decreases from baseline. This compound is also tested in laser-induced hypertensive monkeys, the IOP decreases from baseline.

Compound V is tested in normotensive dogs. The IOP decreases from baseline. This compound is also tested in laser-induced hypertensive monkeys, the IOP decreases from baseline.

Compound VI is tested in normotensive dogs The IOP decreases from baseline. This compound is also tested in laser-induced hypertensive monkeys, the IOP decreases from baseline.

Compound VII is tested in normotensive dogs. The IOP decreases from baseline. This compound is also tested in laser-induced hypertensive monkeys, the IOP decreases from baseline.

Compound VIII is tested in normotensive dogs. The IOP decreases from baseline. This compound is also tested in laser-induced hypertensive monkeys, the IOP decreases from baseline.

Compound IX is tested in normotensive dogs The IOP decreases from baseline. This compound is also tested in laser-induced hypertensive monkeys, the IOP decreases from baseline.

Compound X is tested in normotensive dogs. The IOP decreases from baseline. This compound is also tested in laser-induced hypertensive monkeys, the IOP decreases from baseline.

Compound XI is tested in normotensive dogs. The IOP decreases from baseline. This compound is also tested in laser-induced hypertensive monkeys, the IOP decreases from baseline.

Compound XII is tested in normotensive dogs. The IOP decreases from baseline. This compound is also tested in laser-induced hypertensive monkeys, the IOP decreases from baseline.

Compound XIII is tested in normotensive dogs. The IOP decreases from baseline. This compound is also tested in laser-induced hypertensive monkeys, the IOP decreases from baseline.

Compound XIV is tested in normotensive dogs. The IOP decreases from baseline. This compound is also tested in laser-induced hypertensive monkeys, the IOP decreases from baseline.

Compound XV is tested in normotensive dogs. The IOP decreases from baseline. This compound is also tested in laser-induced hypertensive monkeys, the IOP decreases from baseline.

Compound XVI is tested in normotensive dogs. The IOP decreases from baseline. This compound is also tested in laser-induced hypertensive monkeys, the IOP decreases from baseline.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the appended claims.

What is claimed is:

1. A compound of the formula

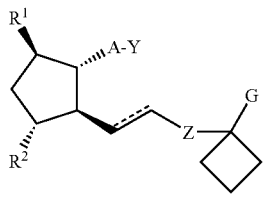

or a pharmaceutically acceptable salt thereof;

Y is

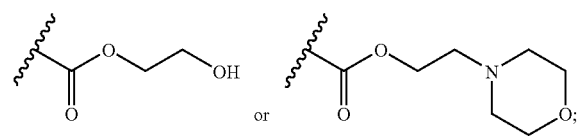

A is —$(CH_2)_6$—, cis —$CH_2CH=CH—(CH_2)_3$—, or —$CH_2C\equiv C—(CH_2)_3$—, wherein 1 or 2 carbon atoms may be replaced by S or O; or A is —$(CH_2)_m$—Ar—$(CH_2)_o$— wherein Ar is interarylene or heterointerarylene, the sum of m and o is 1, 2, 3, or 4, and wherein one $CH_2$ may be replaced by S or O;

$R^1$ is CN or OH;

$R^2$ is H, CN, OH, F, Cl, Br, or $CH_3$ with the proviso that if $R^1$ is OH, $R^2$ is not OH;

Z is $CH_2CHOH$, $CHOHCH_2$, or CHOH;

G is L, $CH_2L$, OL, or SL;

L is phenyl, monocyclic heteroaryl, or $C_{1-6}$ alkyl.

2. The compound of claim 1 of the formula

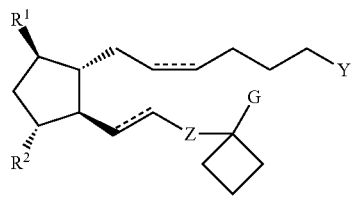

or a pharmaceutically acceptable salt thereof.

3. The compound of claim 1 of the formula

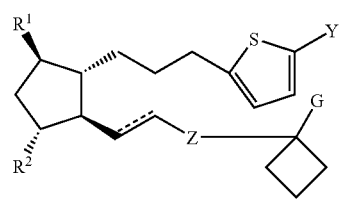

or a pharmaceutically acceptable salt thereof.

4. The compound of claim 1 of the formula

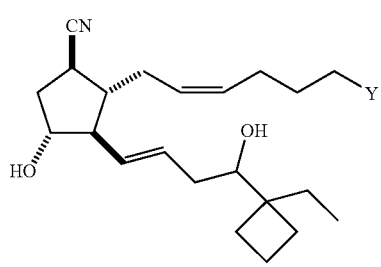

or a pharmaceutically acceptable salt thereof.

5. The compound of claim 1 of the formula

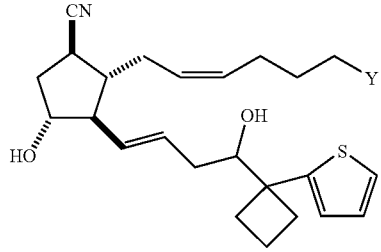

or a pharmaceutically acceptable salt thereof.

6. The compound of claim 1 of the formula

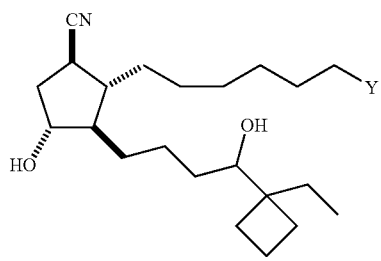

or a pharmaceutically acceptable salt thereof.

7. The compound of claim 1 of the formula

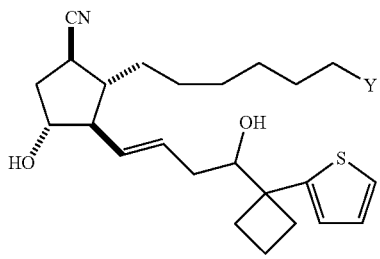

or a pharmaceutically acceptable salt thereof.

8. The compound of claim 1 of the formula

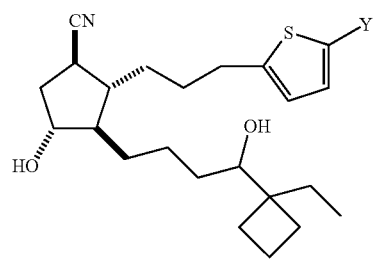

or a pharmaceutically acceptable salt thereof.

9. The compound of claim 1 of the formula

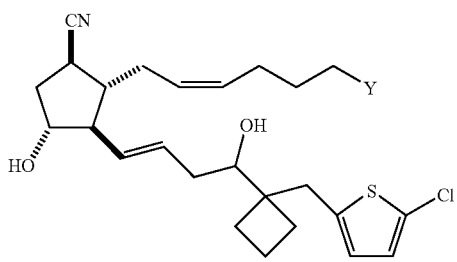

or a pharmaceutically acceptable salt thereof.

10. The compound of claim 1 of the formula

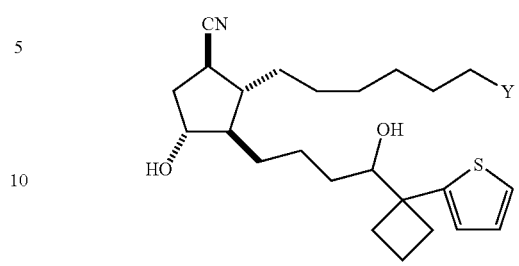

or a pharmaceutically acceptable salt thereof.

11. The compound of claim 1 of the formula

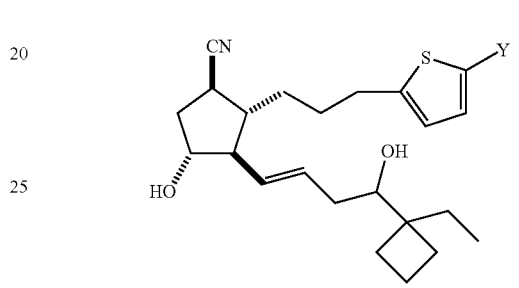

or a pharmaceutically acceptable salt thereof.

12. A method comprising administering a compound according to claim 1 to a mammal for the treatment of glaucoma or ocular hypertension in a mammal.

13. A method comprising administering a compound according to claim 1 to a mammal for the treatment of baldness.

14. A method comprising administering a compound according to claim 1 to a mammal for the stimulation of hair growth.

* * * * *